United States Patent
Beyer et al.

(10) Patent No.: US 12,065,701 B2
(45) Date of Patent: Aug. 20, 2024

(54) IN VITRO METHOD FOR THE DIAGNOSIS OF SYNUCLEINOPATHIES

(71) Applicant: FUNDACIÓ INSTITUT D'INVESTIGACIÓ EN CIÈNCIES DE LA SALUT GERMANS TRIAS I PUJOL, Badalona (ES)

(72) Inventors: Katrin Beyer, Badalona (ES); Francesc Borràs, Badalona (ES); Ana Gámez Valero, Badalona (ES); Ramiro Álvarez, Badalona (ES)

(73) Assignee: FUNDACIÓ INSTITUT D'INVESTIGACIÓ EN CIÈNCIES DE LA SALUT GERMANS TRIAS I PUJOL, Badalona (ES)

( * ) Notice: Subject to any disclaimer, the term of this patent is extended or adjusted under 35 U.S.C. 154(b) by 797 days.

(21) Appl. No.: 17/260,882

(22) PCT Filed: Jul. 19, 2019

(86) PCT No.: PCT/EP2019/069570
§ 371 (c)(1),
(2) Date: Jan. 15, 2021

(87) PCT Pub. No.: WO2020/016437
PCT Pub. Date: Jan. 23, 2020

(65) Prior Publication Data
US 2022/0162699 A1    May 26, 2022

(30) Foreign Application Priority Data
Jul. 19, 2018   (EP) .................................. 18382540

(51) Int. Cl.
*C12Q 1/6883*   (2018.01)
*G01N 33/68*    (2006.01)

(52) U.S. Cl.
CPC ....... *C12Q 1/6883* (2013.01); *G01N 33/6896* (2013.01); *C12Q 2600/112* (2013.01);
(Continued)

(58) Field of Classification Search
None
See application file for complete search history.

(56) References Cited

U.S. PATENT DOCUMENTS

| | | |
|---|---|---|
| 2017/0002423 A1 | 1/2017 | Coppola et al. |
| 2020/0113462 A1 | 4/2020 | Martínez Piñeiro et al. |
| 2020/0354467 A1 | 11/2020 | Sarrias Fornés et al. |

FOREIGN PATENT DOCUMENTS

| | | |
|---|---|---|
| BR | PI0903797-7 A2 | 5/2011 |
| KR | 10-1879392 B1 | 7/2018 |

(Continued)

OTHER PUBLICATIONS

Bijak, M., et al., Platelets miRNA as a Prediction Marker of Thrombotic Episodes, Oct. 4, 2016, Hindawi, 2016, 2872507 (Year: 2016).*

(Continued)

*Primary Examiner* — Joanne Hama
*Assistant Examiner* — Gabrielle A Small
(74) *Attorney, Agent, or Firm* — Seed IP Law Group LLP

(57) ABSTRACT

In vitro method for the diagnosis of synucleinopathies. The present invention is directed to an in vitro method for the specific diagnosis of a synucleinopathy and/or for the differential diagnosis of a synucleinopathy from Alzheimer disease (AD). In a preferred embodiment, the synucleinopathy is Dementia with Lewy bodies (DLB) or Parkinson's disease (PD).

26 Claims, 15 Drawing Sheets

(52) U.S. Cl.
CPC . *C12Q 2600/158* (2013.01); *C12Q 2600/178* (2013.01); *G01N 2800/2835* (2013.01)

(56) References Cited

FOREIGN PATENT DOCUMENTS

| WO | 2011/104023 | A1 |   | 9/2011 |           |
|----|-------------|----|---|--------|-----------|
| WO | 2013/063439 | A1 |   | 5/2013 |           |
| WO | WO-2015091892 | A1 | * | 6/2015 | ........... C12Q 1/6883 |
| WO | 2016/180725 | A1 |   | 11/2016 |          |
| WO | 2016/180726 | A1 |   | 11/2016 |          |

OTHER PUBLICATIONS

Gidlöf, O., et al., Platelets activated during myocardial infarction release functional miRNA, which can be taken up by endothelial cells and regulate ICAM1 expression, May 9, 2013, American Society of Hematology, 121, 3908-3917 (Year: 2013).*

Pordzik, J., et al., The Potential Role of Platelet-Related microRNAs in the Development of Cardiovascular events in High-Risk Populations, Mar. 20, 2018, Frontiers ,9, doi: 10.3389/fendo.2018.00074 (Year: 2018).*

Andrés-León et al., "miRGate: a curated database of human, mouse and rat miRNA-mRNA targets," *Database(2015)*:1-9, 2015.

Ashburner et al., "Gene Ontology: tool for the unification of biology," *Nat Genet. 25*(1):25-29, 2000 (NIH Public Access Author Manuscript, available in PMC Feb. 10, 2011) (9 pages).

Bolger et al., "Trimmomatic: a flexible trimmer for Illumina sequence data," *Bioinformatics 30*(15):2114-2120, 2014.

Dweep et al., "miRWalk2.0: a comprehensive atlas of microRNA-target interactions," *Nature Methods 12*(8):697, 2015 (1 page).

Gibb et al., "A comparison of clinical and pathological features of young- and old-onset Parkinson's disease," *Neurology 38*:1402-1406, 1988.

György et al., "Improved circulating microparticle analysis in acid-citrate dextrose (ACD) anticoagulant tube," *Thrombosis Research 133*:285-292, 2014.

Hsu et al., "miRTarBase update 2014: an information resource for experimentally validated miRNA-target interactions," *Nucleic Acids Research 42*:D78-D85, 2014.

Huang et al., "Systematic and integrative analysis of large gene lists using DAVID Bioinformatics Resources," *Nature Protocols 4*(1):44-57, 2009.

Jiang et al., "miR2Disease: a manually curated database for microRNA deregulation in human disease," *Nucleic Acids Research 37*:D98-D104, 2009.

Khachaturian, "Revised criteria for diagnosis of Alzheimer's disease: National Institute on Aging-Alzheimer's Association diagnostic guidelines for Alzheimer's disease," *Alzheimer's & Dementia 7*:253-256, 2011.

Landry et al., "Existence of a microRNA pathway in anucleate platelets," *Nat Struct Mol Biol. 16*(9):961-966, 2009 (CIHR IRSC Public Access Author Manuscript, available in Jul. 28, 2010) (18 pages).

Langmead et al., "Ultrafast and memory-efficient alignment of short DNA sequences to the human genome," *Genome Biology 10*(3):R25.1-R25.10, 2009.

Li et al., "HMDD v2.0: a database for experimentally supported human microRNA and disease associations," *Nucleic Acids Research 42*:D1070-D1074, 2014.

Lowry, *Concepts & Applications of Inferential Statistics*, Chapter 1.1-Chapter 17.3, 1999-2001, URL=http://vassarstats.net/textbook/ch1pt2.html., Accessed: Mar. 17, 2021, 289 pages.

Lynöe et al., "Informed consent: study of quality of information given to participants in a clinical trial," *BMJ 303*:610-613, 1991.

McKeith et al., "Diagnosis and management of dementia with Lewy bodies: Third report of the DLB Consortium," *Neurology 65*:1863-1872, 2005.

Nelson et al., "MicroRNA expression patterns in human anterior cingulate and motor cortex: A study of dementia with Lewy bodies cases and controls," *Brain Research 1678*:374-383, 2018.

Osman et al., "Characterization of human platelet microRNA by quantitative PCR coupled with an annotation network for predicted target genes," *Platelets 22*(6):433-441, 2011.

Plé et al., "The Repertoire and Features of Human Platelet microRNAs," *PLOS One 7*(12):e50746 2012 (14 pages).

Pundir et al., "Chapter 2. Protein Knowledgebase," *Methods Mol Biol. 1558*:41-55, 2017 (HHS Public Access Author Manuscript, available in Feb. 2, 2018) (22 pages).

Robinson et al., "A scaling normalization method for differential expression analysis of RNA-seq data," *Genome Biology 11*:R25, 2010 (9 pages).

Sáenz-Cuesta et al., "Methods for extracellular vesicles isolation in a hospital setting," *Frontiers in Immunology 6*(50):1-12, 2015.

Singh et al., "Advances in the treatment of Parkinson's disease," *Progress in Neurobiology 81*:29-44, 2007.

Sørensen et al., "miRNA expression profiles in cerebrospinal fluid and blood of patients with Alzheimer's disease and othe types of dementia—an exploratory study," *Translational Neurodegeneration 5*(6):1-12.

Szklarczyk et al., "The STRING database in 2017: quality-controlled protein-protein association networks, made broadly accessible," *Nucleic Acids Research 45*:D362-D368, 2017.

Wang et al., "NSDNA: a manually curated database of experimentally supported ncRNAs associated with nervous system diseases," *Nucleic Acids Research 45*:D902-D907, 2017.

Witwer et al., "Standardization of sample collection, isolation and analysis methods in extracellular vesicle research," *Journal of Extracellular Vesicles 2*:20360, 2013 (25 pages).

Zwicker et al., "Chapter 10: Measurement of Platelet Microparticles," in Gibbins et al. (eds.), Platelets and Megakaryocytes: vol. 3, Additional Protocols and Perspectives, Springer Science & Business, Berlin, Germany, 2012, pp. 127-139.

* cited by examiner

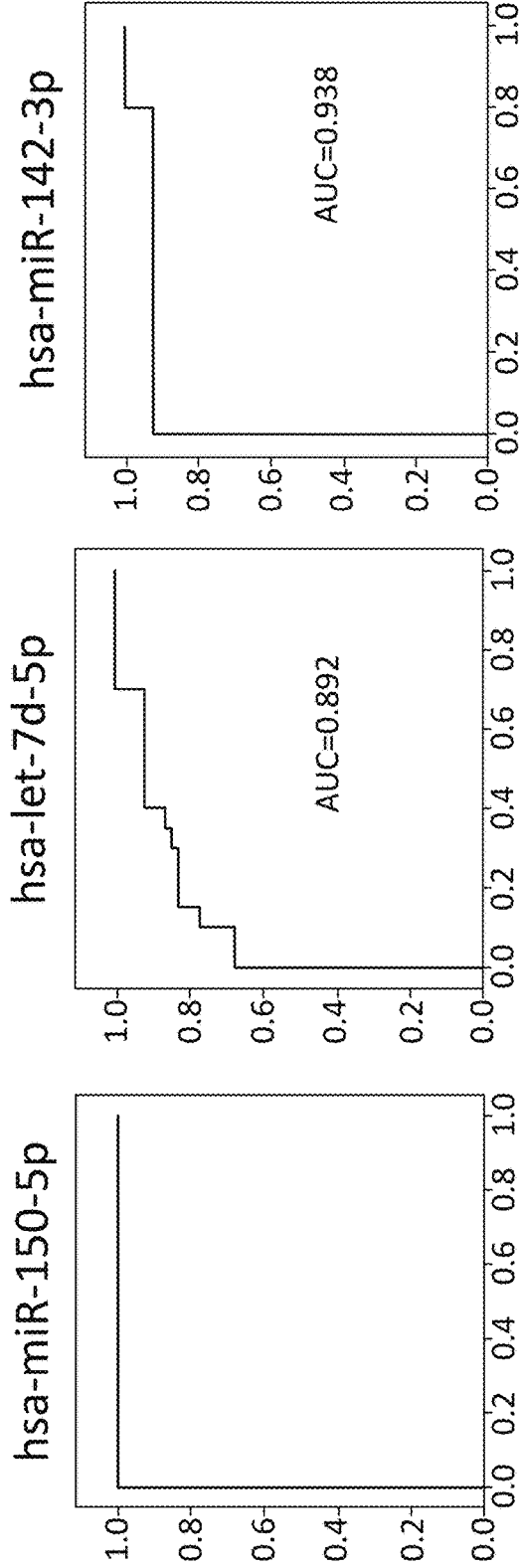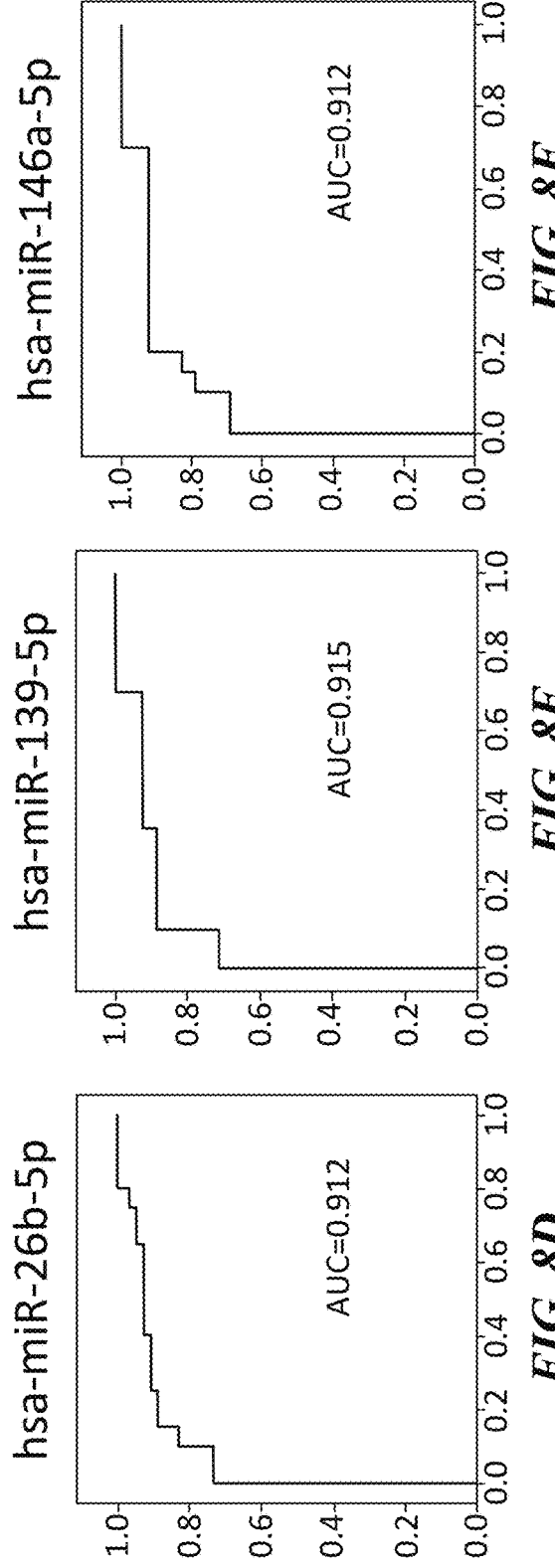

IN VITRO METHOD FOR THE DIAGNOSIS OF SYNUCLEINOPATHIES

FIELD OF THE INVENTION

The present invention refers to the medical field. Particularly, it is directed to an in vitro method for the specific diagnosis of synucleinopathies and/or for the differential diagnosis of synucleinopathies versus Alzheimer disease (AD). In a preferred embodiment, the synucleinopathy which is diagnosed is Dementia with Lewy bodies (DLB) and/or Parkinson's disease (PD).

STATE OF THE ART

DLB is the second most common cause of dementia worldwide after AD and has several common pathological and clinical features with AD and PD. This overlap between these neurodegenerative disorders implies that just 1 of 3 DLB cases is correctly diagnosed.

Dementia is defined as the progressive cognitive decline of sufficient magnitude to interfere with normal social or occupational functions or with the usual daily activities. DLB belongs, together with PD, to the group of Lewy body disorders. Besides Lewy body pathology, DLB brains often contain concomitant AD pathology with β-amyloid and tau depositions, thus DLB present an important overlap with both, PD and AD. About 20-50% of PD patients develop dementia after 10 years of PD diagnosis, being diagnosed as Parkinson's disease with dementia (PDD). Although many advances in the field have allowed improving their characterization, it is still a challenge to early and specifically diagnose DLB, AD and PD. In particular, still up to 80% of DLB cases are missed or misdiagnosed, usually as AD; and the treatment of DLB patients with AD or PD specific therapies can adversely affect their cognition and disease course. For this reason, the identification of biomarkers and molecular features involved in the pathobiology of these disorders for its differential and specific diagnosis is urgently needed.

Moreover, trying to minimize the risk and discomfort of patients, the study of blood has been recently growing, being a promising source of circulating molecules and cell-based biomarkers. In this cell-based scenario, platelets are released into the circulation from the bone marrow after megakaryocytic differentiation essential in processes like homeostasis. Though platelets are anucleate cells, they contain a rough endoplasmic reticulum, ribosomes, a complete mitochondrial and apoptotic system, and display an enzymatic pathway similar to neurons. Thus, research in neurodegenerative diseases has also been conducted through investigation of biological changes and characteristics in platelets. In fact, platelets have been considered along the years a suitable peripheral tissue to study neurodegenerative diseases. The presence of microRNA (miRNA, miR-) in these anucleate cells, converts them also into a promising non-invasive source of miRNAs as biomarkers for several disorders.

Precisely, the present invention is focused on solving the above cited problems by analyzing miRNAs as promising biomarkers for the diagnosis of neurodegenerative diseases and, more specifically, for the specific and/or differential diagnosis of synucleinopathies.

DESCRIPTION OF THE INVENTION

Brief Description of the Invention

The present invention refers to an in vitro method for the specific diagnosis of synucleinopathies and/or for the differential diagnosis of synucleinopathies versus Alzheimer disease (AD). In a preferred embodiment, the synucleinopathy is DLB or PD.

In order to implement the invention, the miRNA content of platelets from DLB (n=7) and healthy controls (n=7) was analyzed using Next-Generation Sequencing (NGS). This analysis resulted in 22 differentially expressed miRNAs between both cohorts, which were validated by quantitative polymerase chain reaction (qPCR) on a different cohort of 14 DLB and 14 control samples. A second validation of 12 best differential miRNAs on independent cohorts, including 10 additional healthy control samples, 12 DLB patients and 10 AD patients was performed. The results showed that, in general, DLB patients have less miRNA expression than controls or AD patients. The 12 validated miRNAs appeared down-regulated in DLB samples, specifically hsa-miR-150-5p. Last, a blind validation using PD samples showed similar expression levels for hsa-miR-150-5p in DLB and PD distinguishing both synucleinopathies from AD and healthy controls. Target gene prediction for hsa-miR-150-5p revealed MYB, EGR2, MUC4 and NOTCH3 among the highest prediction scored. So, the present invention shows hsa-miR-150-5p as a biomarker for the specific diagnosis of synucleinopathies (particularly DLB or PD) versus controls, and/or for the differential diagnosis of synucleinopathies (particularly DLB or PD) versus AD, with an area under the curve of 0.8692 and 1, respectively (see FIG. 4 and FIG. 5).

Although hsa-miR-150-5p, as cited above, is cited in the present invention as a preferred candidate, the present invention offers scientific support (see FIG. 7, FIG. 8, FIG. 9 and FIG. 10), for the use of any of the following miRNAs: miR-7d-5p, miR-142-3p, miR-26b-5p, miR-139-5p, miR-146a-5p, miR-128-3p, miR-6747-3p, miR-132-5p, miR-25-3p, hsa-miR-16-5p or hsa-miR-26a-5p as individual biomarkers for the specific diagnosis of synucleinopathies (particularly DLB or PD) versus controls, and/or for the differential diagnosis of synucleinopathies (particularly DLB or PD) versus AD. Moreover, the present invention also refers to the use of any combination of the above cited 12 biomarkers for the specific diagnosis of synucleinopathies (particularly DLB or PD) versus controls, and/or for the differential diagnosis of synucleinopathies (particularly DLB or PD) versus AD. In a preferred embodiment said combination of miRNAs comprises at least 2, at least 3, at least 4, at least 5, at least 6, at least 7, at least 8, at least 9, at least 10, at least 11 or at least 12 of the following miRNAs: miR-150-5p, miR-7d-5p, miR-142-3p, miR-26b-5p, miR-139-5p, miR-146a-5p, miR-128-3p, miR-6747-3p, miR-132-5p, miR-25-3p, hsa-miR-16-5p or hsa-miR-26a-5p.

Thus hsa-miR-150-5p or, alternatively, any of the following miRNAs: miR-7d-5p, miR-142-3p, miR-26b-5p, miR-139-5p, miR-146a-5p, miR-128-3p, miR-6747-3p, miR-132-5p, miR-25-3p, hsa-miR-16-5p and hsa-miR-26a-5p, or any combination thereof, are identified in the present invention as consistently under-expressed in DLB patients compared to both, AD and controls. Additionally, ROC curves reinforced that hsa-miR-150-5p could be a promising biomarker for DLB rendering 100% specificity and 100% sensibility to differentiate DLB from AD, and around 87% when distinguishing DLB from healthy controls. When samples from PD patients were included, these also showed decreased hsa-miR-150-5p expression that was overlapping with DLB. Hence, it is an indication that this platelet-miRNA has a potential relation to the development of synucleinopathies including both DLB and PD.

Consequently, the present invention provides evidence for the use of miRNA content, preferably from platelets, as promising biomarker source, and proposes the use of any of the miRNAs: hsa-miR-150-5p, miR-7d-5p, miR-142-3p, miR-26b-5p, miR-139-5p, miR-146a-5p, miR-128-3p, miR-6'74'7-3p, miR-132-5p, miR-25-3p, hsa-miR-16-5p or hsa-miR-26a-5p, or any combination thereof, as biomarkers showing a high sensitivity and sensibility, for the differentiation between synucleinopathies, including DLB, and AD. The detection of these miRNAs in platelets or whole blood represents a non-invasive, quick and easy procedure for clinical implementation.

Thus, the first embodiment of the present invention refers to an in vitro method (hereinafter the method of the invention) for the specific diagnosis or prognosis of synucleinopathies, which comprises determining the expression level of at least one of the following miRNAs: hsa-miR-150-5p, miR-7d-5p, miR-142-3p, miR-26b-5p, miR-139-5p, miR-146a-5p, miR-128-3p, miR-6747-3p, miR-132-5p, miR-25-3p, hsa-miR-16-5p or hsa-miR-26a-5p, or any combination thereof, in a biological sample obtained from the patient, wherein a reduced expression level of any of the above cited miRNAs, as compared with the expression level of any of the above cited miRNAs in healthy control subjects, is an indication that the patient is suffering from a synucleinopathy.

The second embodiment of the present invention refers to an in vitro method (hereinafter the method of the invention) for the differential diagnosis of synucleinopathies versus AD, which comprises determining the expression level of at least one of the following miRNAs: hsa-miR-150-5p, miR-7d-5p, miR-142-3p, miR-26b-5p, miR-139-5p, miR-146a-5p, miR-128-3p, miR-6747-3p, miR-132-5p, miR-25-3p, hsa-miR-16-5p or hsa-miR-26a-5p, or any combination thereof, in a biological sample obtained from the patient, wherein a reduced expression level of any of the above cited miRNAs, as compared with the expression level of any of the above cited miRNAs in control patients suffering from AD, is an indication that the subject is suffering from a synucleinopathy and is not suffering from AD.

In a preferred embodiment the present invention refers to an in vitro method for the specific diagnosis or prognosis of DLB and/or PD, which comprises determining the expression level of at least one of the following miRNAs: hsa-miR-150-5p, miR-7d-5p, miR-142-3p, miR-26b-5p, miR-139-5p, miR-146a-5p, miR-128-3p, miR-6747-3p, miR-132-5p, miR-25-3p, hsa-miR-16-5p or hsa-miR-26a-5p, or any combination thereof, in biological samples obtained from the patient, wherein a reduced expression level of any of the above cited miRNAs, as compared with the expression level of any of the above cited miRNAs measured in healthy control subjects, is an indication that the patient is suffering from DLB and/or PD.

In a preferred embodiment the present invention refers to an in vitro method for the differential diagnosis of DLB and/or PD versus AD, which comprises determining the expression level of at least one of the following miRNAs: hsa-miR-150-5p, miR-7d-5p, miR-142-3p, miR-26b-5p, miR-139-5p, miR-146a-5p, miR-128-3p, miR-6747-3p, miR-132-5p, miR-25-3p, hsa-miR-16-5p or hsa-miR-26a-5p, or any combination thereof, in biological samples obtained from the patient, wherein a reduced expression level of any of the above cited miRNAs, as compared with the expression level of any of the above cited miRNAs measured in control patients suffering from AD, is an indication that the subject is suffering from DLB and/or PD and is not suffering from AD.

The third embodiment of the present invention refers to the in vitro use of the expression level of at least one of the following miRNAs: hsa-miR-150-5p, miR-7d-5p, miR-142-3p, miR-26b-5p, miR-139-5p, miR-146a-5p, miR-128-3p, miR-6747-3p, miR-132-5p, miR-25-3p, hsa-miR-16-5p or hsa-miR-26a-5p, or any combination thereof, in biological samples obtained from the patient, for the specific diagnosis or prognosis of synucleinopathies, or the differential diagnosis of synucleinopathies versus Alzheimer disease.

The fourth embodiment of the present invention refers to the in vitro use of a kit comprising reagents for the determination of the expression level of at least one of the following miRNAs: hsa-miR-150-5p, miR-7d-5p, miR-142-3p, miR-26b-5p, miR-139-5p, miR-146a-5p, miR-128-3p, miR-6'74'7-3p, miR-132-5p, miR-25-3p, hsa-miR-16-5p or hsa-miR-26a-5p, or any combination thereof, for the specific diagnosis or prognosis of synucleinopathies, or the differential diagnosis of synucleinopathies versus Alzheimer disease.

In a preferred embodiment the present invention refers to the in vitro use of the expression level of at least one of the following miRNAs: hsa-miR-150-5p, miR-7d-5p, miR-142-3p, miR-26b-5p, miR-139-5p, miR-146a-5p, miR-128-3p, miR-6747-3p, miR-132-5p, miR-25-3p, hsa-miR-16-5p or hsa-miR-26a-5p, or any combination thereof, for the specific diagnosis or prognosis of DLB and/or PD, or the differential diagnosis of DLB and/or PD versus AD.

In a preferred embodiment the present invention refers to the in vitro use of a kit comprising reagents for the determination of the expression level of at least one of the following miRNAs: hsa-miR-150-5p, miR-7d-5p, miR-142-3p, miR-26b-5p, miR-139-5p, miR-146a-5p, miR-128-3p, miR-6'74'7-3p, miR-132-5p, miR-25-3p, hsa-miR-16-5p or hsa-miR-26a-5p, or any combination thereof, for the specific diagnosis or prognosis of DLB and/or PD, or the differential diagnosis of DLB and/or PD versus AD.

In a preferred embodiment the invention refers to the determination of the expression level of at least one of at least hsa-miR-150-5p, preferably in combination with any of the miRNAs comprised in the group: miR-7d-5p, miR-142-3p, miR-26b-5p, miR-139-5p, miR-146a-5p, miR-128-3p, miR-6'74'7-3p, miR-132-5p, miR-25-3p, hsa-miR-16-5p or hsa-miR-26a-5p, for any of the above cited purposes.

In preferred embodiment, the miRNAs are derived from whole blood or platelets.

In a preferred embodiment, the results obtained with the above cited method of the invention are clinically confirmed by other techniques such as: the determination of phosphorylated tau/amyloid beta 1-42 ratio in cerebrospinal fluid and amyloid PET. On the other hand, once the differential diagnosis is carried out with the method of the invention, the fact that the patient is suffering from DLB or PD is clinically confirmed by using techniques such as DaTscan™ (an single-dose, aqueous solution containing 0.07 to 0.13 mcg ioflupane, 74 MBq (2 mCi) iodine-123, 5.8 mg acetic acid, 8.2 mg sodium acetate and 0.05 mL (5%) ethanol).

According to the fifth embodiment of the present invention, the patients diagnosed with the method of the invention can be treated with any of the treatments currently used in the general practice for treating or to provide relief to those patients suffering from synucleinopathies, preferably DLB and/or PD. For example, levodopa (precursor of dopamine), sometimes combined with a dopa decarboxylase inhibitor and sometimes also with a COMT (enzyme which degrades dopamine) inhibitor can be used for treating synucleinopathies, particularly PD. Other examples of treatment that could be used for treating synucleinopathies are dopamine agonists or MAO-B (an enzyme which breaks down dopamine) inhibitors (safinamide, selegiline and rasagiline). Importantly, the use of erroneous treatments arising from misdiagnoses of synucleinopathies, especially DLB, such as neuroleptics for antipsychotic treatment usually used in AD patients can be avoided by the use of the method of the invention. On the other hand, the present invention can be used to identify individuals (e.g. iRBD patients, patients with hyposmia, LRRK2 mutation carriers) who are at elevated risk for developing a synucleinopathy as candidates to receive neuromodulation therapies. Since the development of disease specific neuromodulation treatments is on-going in numerous laboratories, patients identified as classified to undergo this kind of therapies are directly eligible at the moment these are available.

Aggregation of the protein α-synuclein is a key event in the development synucleinopathies, such as DLB and/or PD. So, any compound (including antibodies, vaccines, etc.) which is able to prevent α-synuclein aggregation could be potentially used for treating synucleinopathies, such as DLB and/or PD. Consequently, in preferred embodiment of the present invention, patients suffering from synucleinopathies, preferably DLB and/or PD, who have been diagnosed with any of the methods of the invention, can be treated with alpha-synuclein antiaggregation compounds, for example (non-exhaustive list): BIIB054, NPT200-11/UCB0599, PRX002/RO7046015 or NPT088. So, in a preferred embodiment, the present invention refers to a method for treating patients suffering from synucleinopathies, preferably DLB and/or PD, which comprises the administration of therapeutically effective doses of alpha-synuclein antiaggregation compounds, once they have been diagnosed using any of the methods of the invention, preferably a method which comprises determining the expression level of at least miR-150-5p isolated from platelets obtained from the patient, wherein a reduced expression level of at least the miR-150-5p, as compared with the expression level of at least the miR-150-5p measured in healthy control subjects, is an indication that the patient is suffering from a synucleinopathy. Moreover, the present invention refers to alpha-synuclein antiaggregation therapies for use in the treatment of synucleinopathies, preferably DLB and/or PD, once the patient has been diagnosed by using any of the methods of the invention, preferably a method which comprises determining the expression level of at least miR-150-5p isolated from platelets obtained from the patient, wherein a reduced expression level of at least the miR-150-5p, as compared with the expression level of at least the miR-150-5p measured in healthy control subjects, is an indication that the patient is suffering from a synucleinopathy.

Moreover, the present invention refers to a method for evaluating whether the therapy based on alpha-synuclein antiaggregation compounds is effective, or to a method for assessing whether a patient suffering from synucleinopathies, preferably DLB and/or PD, is responding to a treatment with alpha-synuclein antiaggregation compounds which comprises determining an overexpression of the miRNAs assayed in the present inventions, particularly the miR-150-5p, as compared to the control.

In preferred embodiment, the above cited method of the invention can be performed by determining the expression level of at least one of the miRNAs described above, in combination with any of the biomarkers described in the patent application WO2011104023, which is herein incorporated by reference in its entirety. Specifically, the method of the invention can be performed by determining the expression level of at least one of the miRNAs described above, in combination with the determination of the genotype of the following alterations in butyrylcholinesterase (BChE) gene: the polymorphic site at position 68974 in NCBI Accession Number NG_009031 and/or the polythymine region at positions 4780 to 4786 in NCBI Accession Number NG_00903. The method may further comprise the determination of the genotype of the following alterations in BChE gene: the polymorphic site at position 3687, the polymorphic site at position 4206, and the polymorphic site at position 4443, said positions with reference to NCBI Accession Number NG_009031 (i.e. positions 3687, 4206 and 4443 respectively in SEQ ID NO: 1). Please note that the above cited sequences are disclosed in the patent application WO2011104023 which, as explained above, is herein incorporated by reference in its entirety In a preferred embodiment, the above cited method of the invention can be performed by determining the expression level of at least one of the miRNAs described above, in combination with any of the biomarkers described in the patent application WO2016180725, which is herein incorporated by reference in its entirety. Specifically, the method of the invention can be performed by determining the expression level of at least one of the miRNAs described above, in combination with the detection of at least one variation in SEQ ID NO: 14, or alternatively at least one variation in SEQ ID NO: 15, or alternatively at least one variation in SEQ ID NO: 16, wherein SEQ ID NO: 14, SEQ ID NO: 15 and SEQ ID NO: 16 are comprised within position 175.989.261 to position 176.003.107 in *Homo sapiens* chromosome 5 according to HapMap data release 28 (SEQ ID NO: 1). Please note that the above cited sequences are disclosed in the patent application WO2016180725 which, as explained above, is herein incorporated by reference in its entirety.

In a preferred embodiment, the above cited method of the invention can be performed by determining the expression level of at least one of the miRNAs described above, in combination with any of the biomarkers described in the patent application WO2016180726, which is herein incorporated by reference in its entirety. Specifically, the method of the invention can be performed by determining the expression level of at least one of the miRNAs described above, in combination with the determination of the amount of transcripts SNCAtv3 (SEQ ID NO: 3) and SNCAtv2 (SEQ ID NO: 2) of the human alpha-synuclein gene (SNCA) in a biological sample obtained from the patient, wherein when the amount of both transcripts determined for the patient is reduced with respect to a reference value, this is indicative of the presence of DLB in the patient. Please note that the above cited sequences are disclosed in the patent application WO2016180726 which, as explained above, is herein incorporated by reference in its entirety.

The last embodiment of the present invention refers to a kit, adapted for the diagnosis of synucleinopathies, which comprises:

a) Tools, reagents or media for the isolation of platelets from a biological sample of the patient, and, b) Tools, reagents or media for determining the expression level of at least miR-150-5p.

In a preferred embodiment the kit further comprises reagents or media for determining the expression level of at least one of the miRNAs comprised in the group: miR-7d-5p, miR-142-3p, miR-26b-5p, miR-139-5p, miR-146a-5p, miR-128-3p, miR-6747-3p, miR-132-5p, miR-25-3p, hsa-miR-16-5p or hsa-miR-26a-5p.

On the other hand the present invention also refers to an in vitro method for the diagnosis of AD, which comprises determining the expression level of at least one miRNA included in Table 3, or any combination thereof, isolated from platelets obtained from the patient, wherein an increased expression level of at least one of the miRNAs included in Table 3, as compared with the expression level measured in healthy control subjects, is an indication that the patient is suffering from AD. Thus the present invention also refers to the use of any of the miRNA included in Table 3 for the in vitro diagnosis of AD, and also to a kit comprising a) Tools, reagents or media for the isolation of platelets from a biological sample of the patient, and, b) Tools, reagents or media for determining the expression level of any of the miRNA included in Table 3.

Moreover, the present invention also refers to an in vitro method for the differential diagnosis of DLB from PD, which comprises determining the expression level of at least one miRNA included in Table 4, or any combination thereof, isolated from platelets obtained from the patient, wherein a decreased expression level of at least one of the miRNAs included in Table 4, as compared with the expression level measured in PD patients, is an indication that the patient is suffering from DLB and not from PD. Thus the present invention also refers to the use of any of the miRNA included in Table 4 for the in vitro differential diagnosis of DLB from PD, and also to a kit comprising a) Tools, reagents or media for the isolation of platelets from a biological sample of the patient, and, b) Tools, reagents or media for determining the expression level of any of the miRNA included in Table 4.

For the purpose of the present invention the following terms are defined:

The term "expression level measured in control subjects/patients", when referring to the expression level of the biomarkers (miRNAs) described in the present invention, may refer to two different situations: i) "expression level measured in healthy control subjects" or ii) "expression level measured in control patients suffering from AD". In the first situation i), the subject is likely to suffer from synucleinopathies with a given sensitivity and specificity if the expression level of the biomarker (miRNA) is statistically below said "expression level measured in healthy control subjects". In the second situation ii), the subject is likely to suffer from synucleinopathies, and not from AD, with a given sensitivity and specificity if the expression level of the biomarker (miRNA) is statistically below said "expression level measured in control patients suffering from AD". Thus, it can be said that in the present invention two different "reference values" are used: i) "expression level measured in healthy control subjects" for carrying out a "specific diagnosis" or ii) "expression level measured in control patients suffering from AD" for carrying out a "differential diagnosis".

A "reference value" can be a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Preferably, the person skilled in the art may compare the biomarker levels (or scores) obtained according to the method of the invention with a defined threshold value. Typically, the optimal sensitivity and specificity (and so the threshold value) can be determined using a Receiver Operating Characteristic (ROC) curve based on experimental data. For example, after determining the levels of the biomarkers in a group of reference, one can use algorithmic analysis for the statistic treatment of the measured concentrations of biomarkers in biological samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-speciftcity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc® 9.2.0.1 medical statistical software, SPSS® 9.0 (Statistical Package for the Social Sciences) (IBM, Armonk, USA).

"Specific diagnosis or diagnosis" as used in the present invention refers just to the identification of synucleinopathies in a subject. In order to do so, the level of expression of the miRNAs isolated from the patient is compared with the "expression level measured in healthy control subjects".

"Differential diagnosis" as used in the present invention is aimed at distinguishing a particular disease or condition such as synucleinopathies from others that present similar clinical features like AD. In order to do so, the level of expression of the miRNAs isolated from the patient is compared with the "expression level measured in control patients suffering from AD".

The term "synucleinopathy or synucleinopathies" refers to neurodegenerative diseases characterized by the abnormal accumulation of aggregates of alpha-synuclein protein in neurons, nerve fibres or glial cells. There are three main types of synucleinopathy: PD, DLB, and multiple system atrophy (MSA).

The term "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

DESCRIPTION OF THE FIGURES

FIGS. 8A-8J. miRNA expression in platelets. ROC curves of the miRNAs: hsa-miR-150-5p, hsa-let-7d-5p, hsa-miR-142-3p, hsa-miR-26b-5p, hsa-miR-139-5p, hsa-miR-146-5p, hsa-miR-128-3p, hsa-miR-6747-3p, hsa-miR-132-5p and hsa-miR-25-3p for the differentiation of DLB versus AD. X axis: specificity. Y axis: sensitivity.

DETAILED DESCRIPTION OF THE INVENTION

Example 1. Patients

Figure 1:
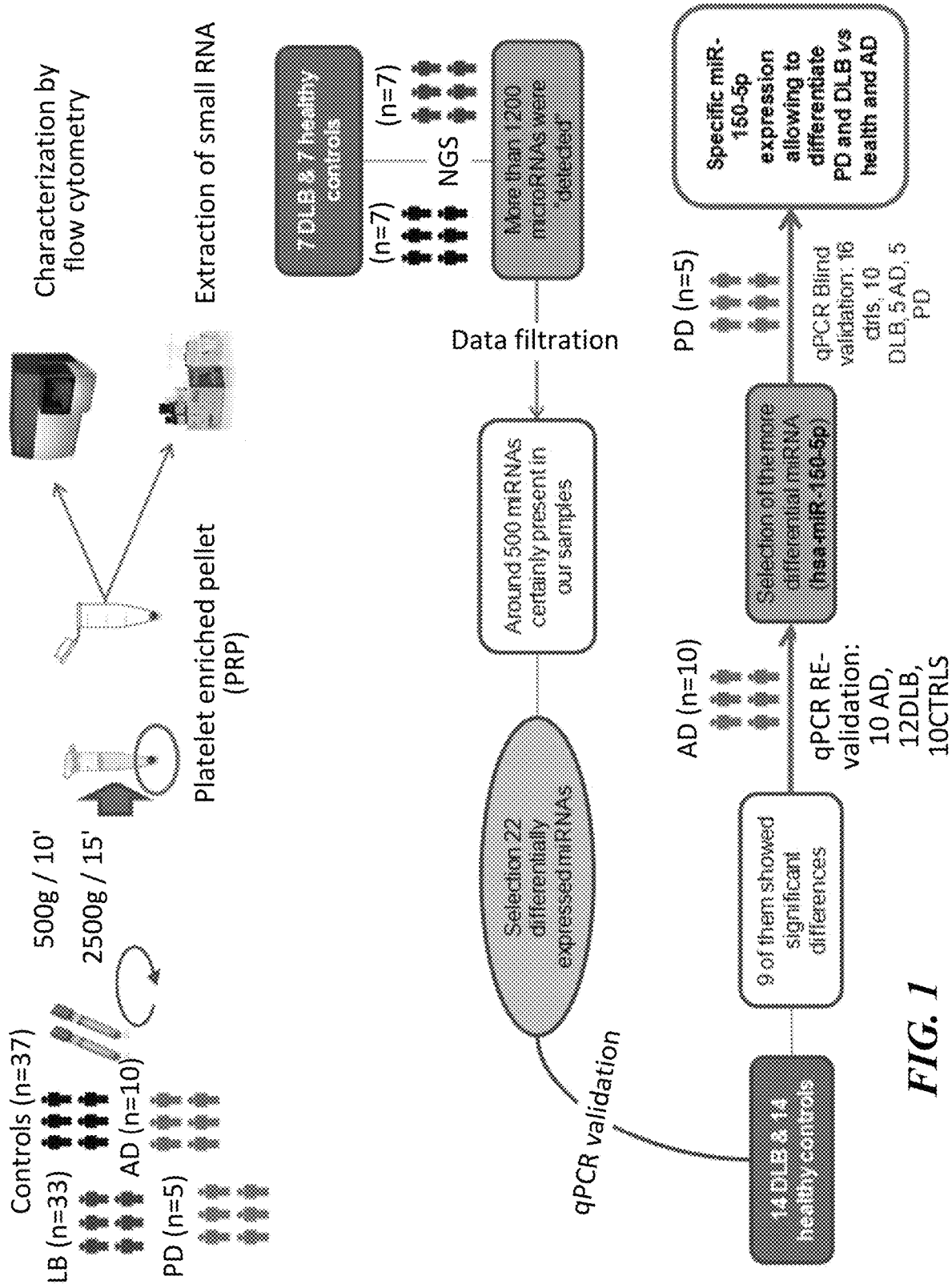
FIG. 1. Complete workflow of the current study. After isolation and characterization of platelet-enriched pellets, NGS was applied and several qPCR validation phases were carried out.

Thirty-three DLB patients (age range 57-86 years; mean 71.8 years; male:female ratio 1.4:1) from the Universitary Bellvitge Hospital, (L'Hospitalet de Llobregat, Barcelona), and 37 age- and gender-matched healthy control individuals (age-range 61-85; mean 72.02 years; male:female 0.8:1) from the same hospital and the University Hospital Germans Trias i Pujol (Badalona, Barcelona), were included in this study. DLB patients were diagnosed according to the 2005 DLB Consortium criteria [McKeith I G, Dickson D W, Lowe J, Emre M, O'Brien J T, Feldman H, et al. *Diagnosis and management of dementia with Lewy bodies: third report of the DLB Consortium. Neurology* 2005; 65:1863-72] and age at onset was defined as the age when memory loss or parkinsonism was first noticed by relatives. A third cohort of 10 AD patients (age range 65-85; mean 73.9; male:female ratio 1.5) with a Global Deterioration Scale of 4.3±1.2 degrees, was also recruited. AD diagnosis was assessed in the University Hospital Germans Trias i Pujol (Badalona, Barcelona) following the 2011-revised criteria from the National Institute on Aging and the Alzheimer's Association [Khachaturian Z S. *Revised criteria for diagnosis of Alzheimer's disease: National Institute on Aging-Alzheimer's Association diagnostic guidelines for Alzheimer's disease. Alzh Dement* 2011; 7(3):253-6]. Thirteen non-demented PD patients (age range 42-87 years; mean 66.9 years; male:female ratio 2.5:1) were also recruited in the same hospital for the final validation assay. PD diagnosis was assessed by the UK PD Society Brain Bank criteria [Gibb W, Lees A. *A comparison of clinical and pathological features of young-and old-onset Parkinson's disease. Neurology* 1988; 38:1402-06]. The following protocol was approved by the Clinical Research Ethics Committee of our institution and conducted according to the Declaration of Helsinki Principles [Lynöe N, Sandlund M, Dahlqvist G, Jacobsson L. *Informed consent: study of quality of information given to participants in a clinical trial. BMJ* 1991; 303:610-13]. Written informed consent was obtained from each subject.

Example 2. Blood Collection, Purification and Characterization of Platelets

Peripheral blood was collected following standard procedures to minimize coagulation and platelet activation [Zwicker J I, Lacroix R, Dignat-george F, Furie B C, Furie B. *Platelets and Megakaryocytes. Methods* 2012; 788:127-39; Witwer K W, Buzás E I, Bemis L T, Bora A, Lässer C, Lótvall J, et al. *Standardization of sample collection, isolation and analysis methods in extracellular vesicle research. J Extracell Vesicles* 2013; 2: 1-25; György B, Pálóczi K, Kovács A, Barabás E, Bekö G, Várnai K, et al. *Improved circulating microparticle analysis in acid-citrate dextrose (ACD) anticoagulant tube, Thromb Res* 2014; 133:285-92]. Briefly, after venous puncture, 12-15 mL of blood were collected in sodium citrate pre-treated tubes (BD Vacutainer®, New Jersey, USA), and processed within the 2 hours following the collection. After centrifugation at 500×g for 10 minutes at room temperature to minimize contamination by red blood cells and leukocytes, centrifugation at 2,500 ×g for 15 minutes at room temperature [Sáenz-Cuesta M, Arbelaiz A, Oregi A, Irizar H, Osorio-Querejeta I, Muñoz-Culla M, et al. *Methods for extracellular vesicles isolation in a hospital setting. Front in Immunology* 2015; 6(50)] was performed in order to obtain a platelet-enriched pellet. The pellet was res-suspended in 250 μL of PBS and characterized by flow cytometry. 50 μL of the samples were incubated for 15 min at room temperature with 5 μL of CD61-FITC antibody, as platelets marker, and 5 μL CD45-APC antibodies in order to detect possibly leukocyte contamination. The samples were then frozen and kept at −80° C. until processing and miRNA isolation.

Example 3. Extraction of Platelet Derived Small RNA

Platelet-enriched pellet obtained post centrifugation at 2,500×g for 15 minutes were thawed slowly on ice previous miRNA isolation. miRNA extraction was performed using mirVana™ PARIS™ Kit (kit employing Ambion® PARIS (Protein And RNA Isolation System) to recover both native protein and RNA from same sample) (Invitrogen, Carlsbad, USA) at room temperature as described by the manufacturers. Briefly, 600 μL of lysis buffer and ⅒ of miRNA Homogenate Additive Mix were added to each pellet and incubated after vortexing for 10 minutes on ice. After adding one volume of phenol-chloroform and mixing, centrifugation at 10,000×g for 5 minutes was performed. One third and ⅔ volume of ethanol was added in 2 consecutive steps to the miRNA containing aqueous phase, and passed through a filter column. After corresponding washing steps, miRNAs were eluted with 100 μL of elution buffer. The extracted material was kept on ice and frozen at −80° C. until forthcoming analysis.

Example 4. MicroRNA Isolation from Whole Blood

RNA isolation was carried out after collection of 3 ml of whole blood in PAXgene® Blood RNA tubes (16×100 mm plastic tube with draw volume of 2.5 mL capable of stabilizing intracellular RNA for up to three days at room temperature or for five days at 2-8°) C. (PreAnalytiX, Hombrechtikon, Switzerland) by the use of the PAXgene® Blood miRNA Kit 50, v2 (kit for 50 RNA preparations) (PreAnalytiX, Hombrechtikon, Switzerland) following manufacturer's instructions. RNA quantity, purity and integrity were ascertained by the Agilent 2100 BIOANALYZER® (Agilent Technologies, Santa Clara, USA).

Example 5. Discovery Phase: MicroRNA Sequencing and Sequencing Data Analysis The total volume of the obtained miRNAs from 7 DLB and 7 control samples was precipitated overnight at −20° C. with 1 μL of glycogen (20 μg/μL), 10% 3 M AcNa (ph 4.8) and 2 volumes of ethanol. miRNAs were resuspended in 10 μL RNase free H$_2$O and heated at 65° C. for 2-3 min. Quality control and size distribution of the purified small RNA was assessed by Bioanalyzer 2100 (Agilent Technologies, Santa Clara, USA).

Six μL of each sample (n=7 DLB samples; n=7 control samples) were used for library preparation with NEBNext® Multiplex Small RNA Sample Preparation Set for Illumina (New England Biolabs, Ipswich, USA) following manufacturer's instructions. Individual libraries were subjected to the quality analysis using a D1000 ScreenTape (TapeStation, Agilent Technologies, Santa Clara, USA), quantified by fluorimetry and pooled. Clustering and sequencing were performed on an Illumina MiSeq™ Sequencer (benchtop sequencing system) (Illumina, San Diego, USA) at 1×50c single read mode and 200,000 reads were obtained for each sample.

FASTQ® (text file containing sequence data) Q raw data obtained from the Illumina MiSeq™ Sequencer were analyzed as follow. Firstly, adapter sequences from the obtained reads were removed using Trimmomatic [Bolger AM, Lohse M, Usadel B. *Trimmomatic: a flexible trimmer for Illumina sequence data. Bioinformatics* 2014; 30: 2114-20] and reads were mapped to miRNA sequences using the Bowtie2 algorithm [Langmead B, Trapnell C, Pop M, Salzberg SL. Ultrafast and memory-efficient alignment of short DNA sequences to the human genome. Genome Biol 2009; 10(3): R25]. For each sample, the number of reads matched with a particular miRNA sequence was counted and the final count matrix was normalized through the weighted trimmed means of M-values (TMM) [Robinson MD, Oshlack A. A scaling normalization method for differential expression analysis of RNA-seq data Genome Biol 2010; 11(3):R25]. For possible biomarker selection the following criteria had to be fulfilled: (a) Minimum of 5 reads per sample; (b) Present in all patient samples and absent (less than 5 reads) in more than the half of the control samples; (c) Present in all control samples and absent in more than the half of the patient samples. In all the cases, and when a miRNAs was present in both cohorts, differential expression analyses were carried through applying the Lilliefors' composite goodness-of-fit test, Jarque-Bera hypothesis test and Shapiro-Wilk test to test if the samples fitted normal distributions; and the Wilconxon-rank sum test (p-value <0.05) [Lowry R. *Concepts & Applications of Inferential Statistics*. Retrieved Mar. 9, 2011 was used to determine whether miRNAs were differentially expressed between both cohorts. Validation process of the differences obtained was analyzed by the methodology Leave-One-Out (LOO) cross-validation.

Example 6. Validation Phase: Reverse Transcription and Quantitative Real-Time PCR miRNA was reverse-transcribed using MIRCURY LNA™ Universal cDNA synthesis Kit II (Exiqon A/S, Vedbaek, Denmark) according to the manufacturer's protocol. RNA concentration was adjusted to 5 ng/μL with nuclease free water and mixed with the reaction buffer and enzyme mix according to the working volume specified in the instruction manual. Retro-transcription reaction took place at 42° C. for 60 minutes and enzymatic activity was stopped at 95° C. for 5 min. cDNA mixture was diluted 1:80 and 4 μL were used for the quantitative PCR (qPCR) reactions with ExiLENT SYBR™ Green Master Mix (PCR kit for use with the MIRCURY LNA™ Universal cDNA synthesis Kit) (Exiqon A/S, Vedbaek, Denmark) following manufacturer's indications on a LightCycler® 480 (plate-based real-time PCR device for gene detection, gene expression analysis, genetic variation analysis, and array data validation) (Roche, Basel, Switzerland). Samples were set up in duplicates, miRNA spike-in UniSp6 was used as control for the retrotranscription. miRNA LNA technology Pick-&-Mix™ PCR pre-designed panels (Exiqon A/S, Vedbaek, Denmark) with miRNA UniSp3 as interplate calibrator control were used.

Example 7. Statistical Analysis

Values for NGS data and reads are given as mean±SD. Expression levels of the miRNAs selected for qPCR validation were determined using crossing point (Cp) values. Cp values were averaged between duplicates and normalized against UniSp6 spike-in Cp values for platelet derived miRNA and against hsa-miR-191-5p in the case of whole blood. Relative expression in DLB, AD and PD was estimated respect to healthy controls and represented as fold expression changes as obtained by $2^{-\Delta\Delta Cp}$. Statistical analyses were performed using GRAPHPADPRISM® 7 (GraphPad Software, Inc., La Jolla, CA, USA). Two-tailed unpaired T-test was applied individually for each miRNA analyzed to compare Cp values between control and DLB groups. When comparing more than two groups (DLB, controls, AD and PD), multiple comparisons were performed applying Kruskal-Wallis non-parametric test. In all cases, confidence interval of 95% and a p-value below 0.05 was considered to be significant. To assess the diagnostic potential, the area under the ROC curve (AUC) was calculated for each miRNA using SPSS Statistics 15 (IBM, Armonk, NY, USA) and GRAPHPADPRISM® 7 in order to determine the diagnostic and characterization sensitivity and specificity (95 % C.I., AUC >0.750 was considered as minimum value for a miRNA to be defined as good biomarker).

Example 8. MiRNA Target Prediction and Analysis

Biomarker candidates obtained from NGS were sought in several databases and relation with dementia with Lewy bodies and others neurodegenerative disorders (PD, AD, mild cognitive impairment, vascular dementia, multiple sclerosis, amyotrophic lateral sclerosis, Huntington's disease and progressive supranuclear palsy) was assessed through a manual bibliographic search in PubMed, The Nervous System Disease NcRNAome Atlas (NSDNA) [Wang J, Cao Y, Zhang H, Wang T, Tian Q, Lu X et al. *NSDNA: a manually curated database of experimentally supported ncRNAs associated with nervous system diseases. Nucleic Acids Res* 2017; 45(D1):D902-D907], miR2Disease database [Jiang Q, Wang Y, Hao Y, Juan L, Teng M, Zhang X, et al. *miR2Disease: a manually curated database for microRNA deregulation in human disease. Nucleic Acids Res* 2009; 37: *D*98-104] and the Human microRNA Disease Database (HMDD) [Li Y, Qiu C, Tu J, Geng B, Yang J, Jiang T, et al. HMDD v 2.0: a database for experimentally supported human microRNA and disease associations. Nucleic Acids Res 2014; 42:D1070-4].

Hsa-miR-150-5p possible targets were predicted using MirWalk 2.0 [Dweep H, Gretz N. *miRWalk2.0: a comprehensive atlas of microRNA-target interactions. Nature Methods* 2015; 12(8): 697], miRGate [Andrés-León E, Gómez-López G, Pisano D G. *miRGate: a curated database of human, mouse and rat miRNA-mRNA targets. Database* (Oxford) 2015; 8;2015:bav035] and miRTarBase [Hsu S D, Tseng Y T, Shrestha S, Lin Y L, Khaleel A, Chou C H, et al. *miRTarBase update 2014: an information resource for experimentally validated miRNA-target interactions. Nucleic Acids Res* 2014; 42:D78-D85] databases. Relation among the confirmed predicted targets was analyzed with String DataBase [Szklarczyk D, Morris J H, Cook H, Kuhn M, Wyder S, Simonovic M, et al. The STRING database in 2017: quality-controlled protein protein association networks, made broadly accessible. *Nucleic Acids Res* 2017; 45:D362-68] and GO consortium online tool [Ashburner M, Ball C A, Blake J A, Botstein D, Butler H, Cherry J M, et al. *Gene ontology: tool for the unification of biology. Nat Genet* 2000; 25(1):25-9; *Gene Ontology Consortium,* 2017] obtaining related biological processes, cellular components and KEEG Pathways. Gene description and main information were screened through Uniprot database [Pundir S, Martin M J, O'Donovan C. *UniProt Protein Knowledgebase. Methods Mol Biol* 2017; 1558:41-55]. As well, DAVID database [Huang D W, Sherman B T, Lempicki R A. *Systematic and integrative analysis of large gene lists using DAVID Bioinformatics Resources. Nature Protoc* 2009; 4(1):44-57] was used to obtain a clustered network based on involved KEEG pathways and related diseases with a Fisher's exact p-value assigned to each miRNA-process relation (the cut off EASE—Expression Analysis Systematic Explorer—was set as default at 0.1).

The whole workflow of this study is shown in FIG. 1.

Example 9. Platelet Characterization and miRNA Profile Discovery

Figure 2:
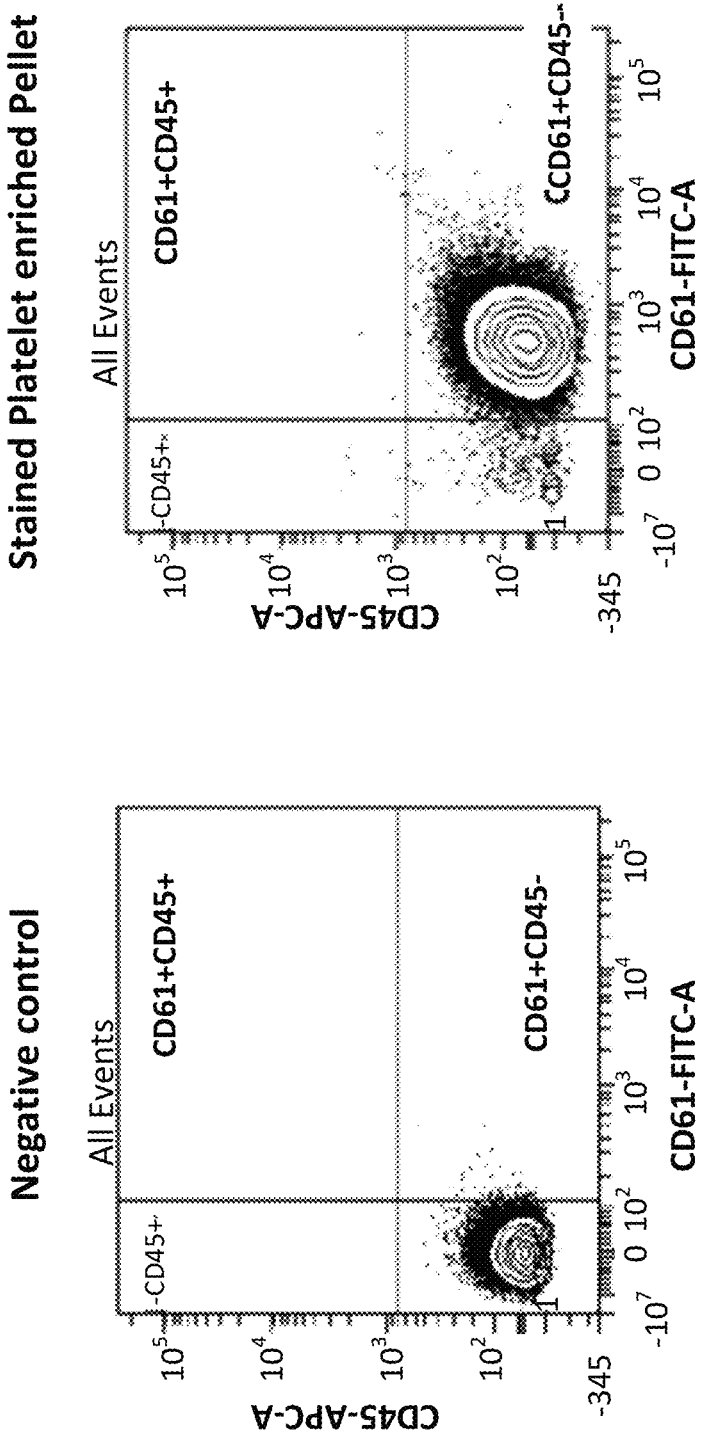
FIG. 2. Platelet-enriched pellet characterization by flow cytometry. CD61 staining was performed to identify platelets and CD45 was used as leukocyte marker for staining of leukocyte contamination. Negative control with no CD61 staining (left); CD61-positive and CD45-negative staining is observed in platelet enriched pellet (right).

Characterization of the platelet-enriched pellet obtained after serial centrifugations for possibly leukocyte contamination did not show almost staining for the leukocyte marker CD45 in our samples. Instead, a high fluorescent signal for the platelet marker CD61 was obtained (FIG. 2).

After small RNA extraction, bioanalyzer analysis showed an enriched profile of 20-40 nucleotides molecules characteristic of small RNA and miRNA which were used to construct libraries by NGS. NGS generated a mean total of 3,437,293 raw reads sized around 65-75 nucleotides (taking into account the ligated adapters). After raw data processing and adapter removal, the mapping by Bowtie algorithm reported an average of 1,488,791±348,407 reads per sample in the control group, and 1,210,616±706,346 reads per DLB sample that mapped to already known 1,279 different mature miRNA molecules. From those, 534 miRNAs met the previously established criteria for the minimum number of reads. Taking into account the precursor immature forms of our data set (no −5p or −3p forms consideration), 430 different precursors-miRNAs was compared with the available literature in platelet-miRNA content. From those, 304 had already been described as associated to platelets. Of all mature miRNAs identified, 58.9% had been already described in the first platelet-miRNA profiling studies [Landry P, Plante I, Ouellet D L, Perron M P, Rousseau G, Provost P. *Existence of a microRNA pathway in anucleate platelets. Nat Struct Mol Biol* 2009; 16:961-66]; [Osman A, Falker K. *Characterization of human platelet microRNA by quantitative PCR coupled with an annotation network for predicted target genes. Platelets* 2011; 22:433-41]. It was also found that the most representative miRNA families described in platelets, such as let-7 family or miR-103, miR-21 groups [Plé H, Landry P, Benham A, Coarfa C, Gunaratne P H, Provost P. *The repertoire and features of human platelet microRNAs. PlOs One* 2012; 7:e50746], were also the most representative in our analysis.

The normalized counts from NGS data were analyzed using the Wilconxon-rank sum test (threshold p-value set at 0.05) and a total of 22 miRNAs showing good classifier capability and differentially expressed between DLB and healthy control cohorts, were selected for further validation by qPCR (hsa-miR-1343-3p, hsa-miR-191-3p, hsa-miR-6747-3p, hsa-miR-504-5p, hsa-miR-6741-3p, hsa-miR-128-

3p, hsa-miR-1468-5p, hsa-miR-139-5p, hsa-let-7d-5p, hsa-let-7d-3p, hsa-miR-142-3p, hsa-miR-132-5p, hsa-miR-150-5p, hsa-miR-23a-5p, hsa-miR-26b-5p, hsa-miR-1301-3p, hsa-miR-625-3p, hsa-miR-146a-5p, hsa-miR-25-3p, hsa-miR-877-3p, hsa-miR-1908-5p, hsa-miR-744-5p).

Example 10. Validation of miRNA Expression

Figure 3A:
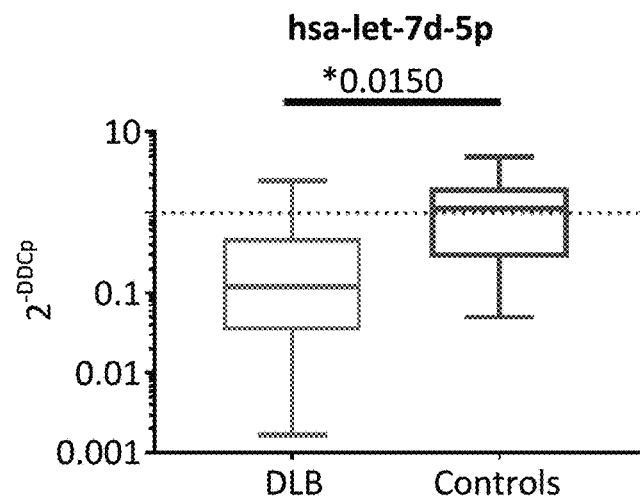
FIGS. 3A-3C. miRNAs expression in DLB and controls. Expression of three miRNAs is shown as example of diminished miRNA expression found in DLB compared to controls. Overlapping expression levels were also found.
Figure 3B:
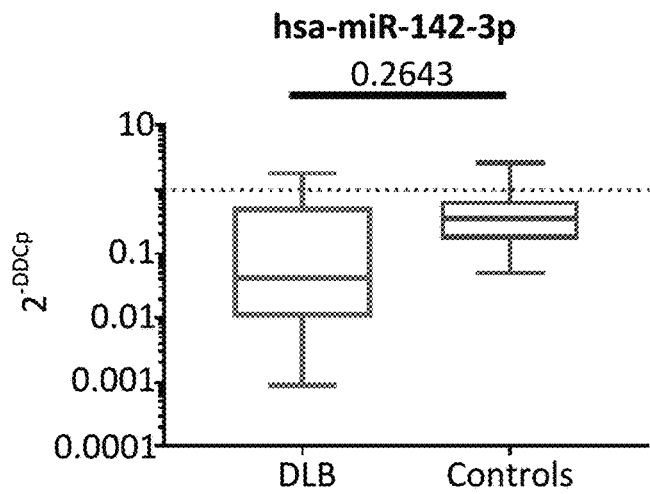
Figure 3C:
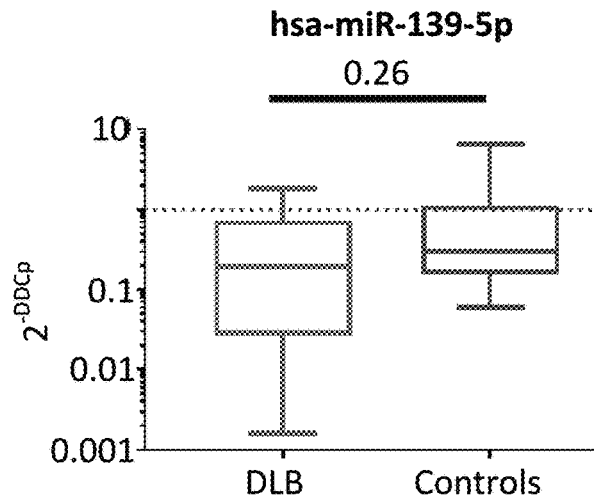
Figure 4:
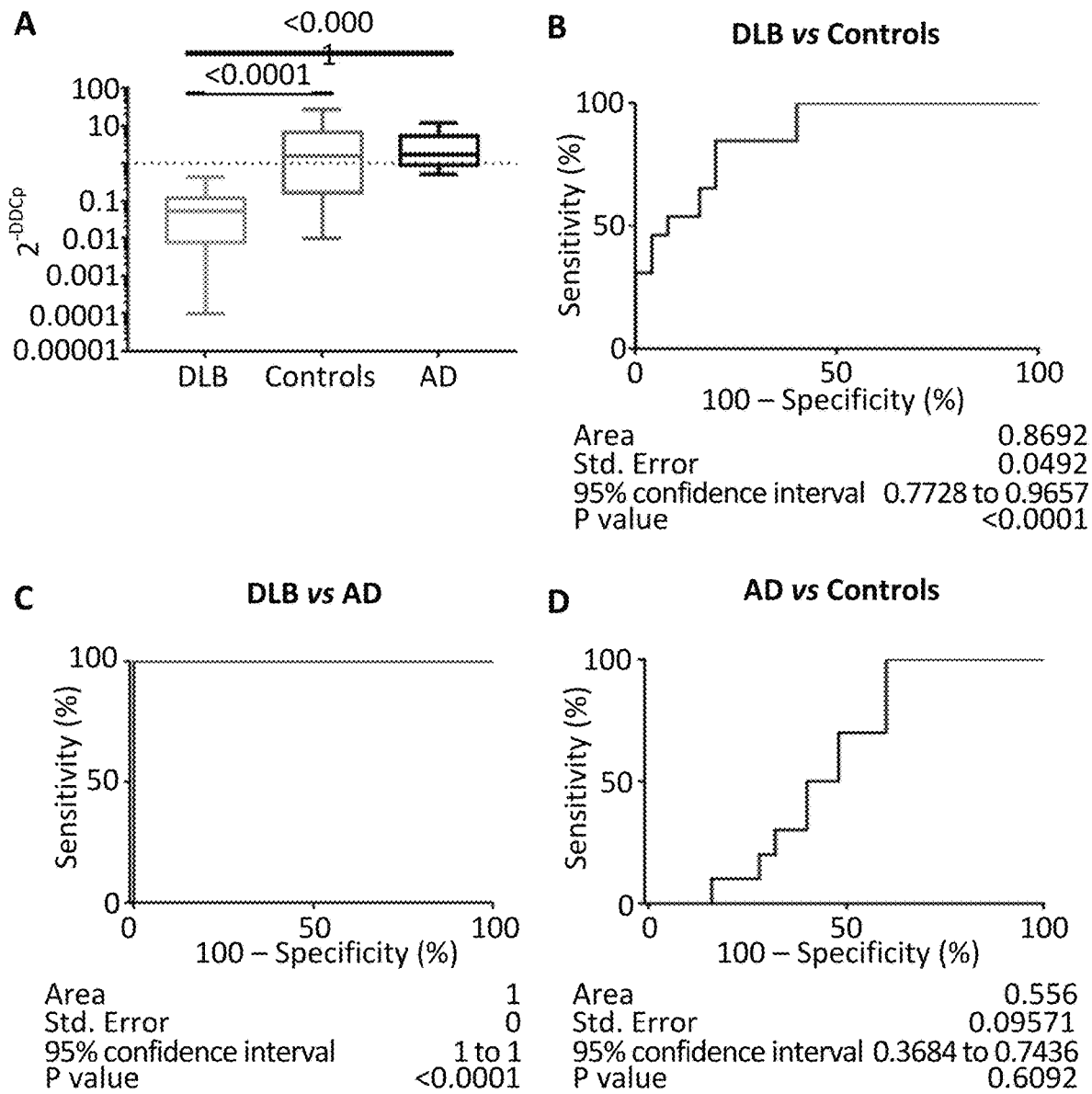
FIGS. 4A-4D. hsa-miR-150-5p expression in DLB, AD and controls. (A) Fold change expression by qPCR. (B) ROC curve for the differential identification of DLB cases vs control samples. (C) ROC curve for the differentiation of DLB and AD. (D) ROC curve for the differentiation of AD and healthy controls.

The selected 22 differentially expressed miRNAs were validated by qPCR in independent DLB and control cohorts, each constituted of 14 individuals. The majority of the validated miRNAs were down-regulated in the DLB group compared to controls as shown in FIG. 3 for three of the most representative. Among those, the most important decrease was found for hsa-miR-150-5p in DLB vs controls (0.03±0.01 vs. 0.76±0.34; p<0.0001). Then, the 12 miRNAs more differentially expressed between both cohorts (hsa-miR-150-5p, hsa-miR-7d-5p, hsa-miR-142-3p, hsa-miR-26b-5p, hsa-miR-139-5p, hsa-miR-146a-5p, hsa-miR-128-3p, hsa-miR-6747-3p, hsa-miR-132-5p, miR-25-3p, hsa-miR-16-5p or hsa-miR-26a-5p) underwent an additional qPCR-validation in independent cohorts of 12 DLB and 10 controls from a different hospital, and where a group of 10 AD patients was also included. Expression levels for all miRNAs tested in AD were similar to control samples and greatly differed from DLB. The previous results for hsa-miR-150-5p expression levels were confirmed as it was repeatedly significantly decreased in DLB compared to controls, but also compared to AD samples (p<0.0001 and p=0.0047, respectively). The ensemble of both qPCR-analyses is represented in FIG. 4A. ROC curves taking into account fold changes for each cohort were calculated. A ROC curve with AUC=0.8692 was obtained for the specificity and sensibility distinguishing between controls (n=24) and DLB samples (n=26) (FIG. 4B). When AD (n=10) and DLB (n=26) were considered, AUC=1 ROC curve was obtained (FIG. 4C). No significant sensibility and specificity was reached for the determination of AD compared to healthy controls (FIG. 4D).

Example 11. Blind Validation Including PD Patients

Figure 5:
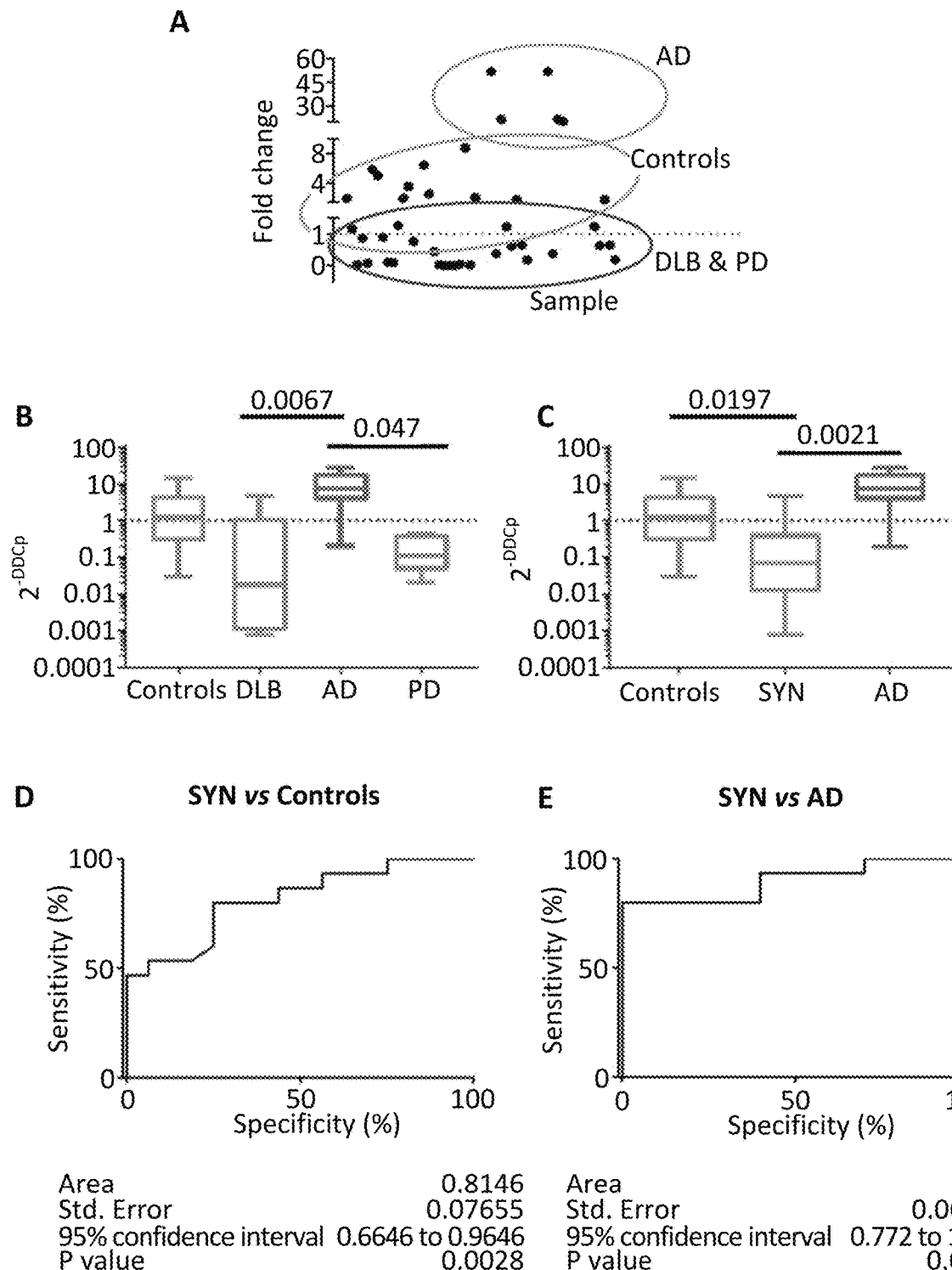
FIGS. 5A-5E. Diagnostic outcome for hsa-miR-150-5p as biomarker. Blind validation including PD samples was performed. (A) Expression changes were similar in PD and DLB (blue circle), differed from AD (green circle), and partially overlapped with healthy controls (orange circle). (B) Higher expression levels for hsa-miR-150-5p were observed in AD compared to DLB and PD samples (n=10 DLB, n=5 AD, n=5 PD and n=16 controls). (C) DLB and PD were analyzed together as synucleinopathies. In all the cases, mean and SD are plotted. (D) ROC curve for the differentiation of synucleinopathies and controls. (E) ROC curve for the differentiation of synucleinopathies and AD.

Then, we analyzed the expression of hsa-miR-150-5p in a blind qPCR where 16 controls (4 new, not previously analyzed), 10 DLB (5 independent new samples), 5 non-demented PD and 5 of the AD patients were included. Results were analyzed by two independent researchers who did not know the identity of the samples and were grouped into low- and high- hsa-miR-150-5p expressing. After sample identification, DLB and PD were localized within the low- hsa-miR-150-5p expressing region and AD within the high- hsa-miR-150-5p expressing region. Hsa-miR-150-5p expression in controls was overlapping with both, AD and DLB/PD (FIG. 5A). Expression levels differed significantly between DLB and AD (p=0.0067), and also between PD and AD (p=0.047) (FIG. 5B). When DLB and PD were grouped as synucleinopathies, significant differences were observed compared to the control and AD groups (p=0.02 and p=0.002, respectively) (FIG. 5C). ROC curves displayed a high sensitivity and specificity for the differentiation between synucleinopathies and controls (AUC=0.8146) and AD (AUC=0.9) (FIGS. 5D and 5E).

Example 12. Clinical Stratification Panel Based on hsa-miR-150-5p

Based upon these results, hsa-miR-150-5p expression in platelet-enriched pellets could be considered a plausible biomarker for the differential diagnosis of DLB vs AD with an easy application in clinical settings. In PCR-based analysis, Cp or crossing point, which inversely correlates with gene expression, corresponds to the number of cycles needed for the amplification-associated fluorescence to reach a specific threshold. Hence, considering qPCR-Cp values after reaction in a LightCycler480 (Initial heat activation at 95° C./2 min; 45 cycles: 10 s at 95° C., 60 at 56° C.; and melting curve analysis from 60-95° C.), it is possible to assess a Cp-based stratification panel for samples' classification as exposed in Table 1.

TABLE 1

Cp values for hsa-miR-150-5p expression determination by qPCR.

| Stage | Expected Cp |
|---|---|
| Healthy Control | 20-25 |
| AD | 19-23 |
| DLB | 23-31 |
| PD | 21-23 |
| Healthy Control | 20-25 |
| AD | 19-23 |
| Synucleinopathy | 23-29 |

Example 13. Hsa-miR-150-5p Target Prediction

Figure 6A:
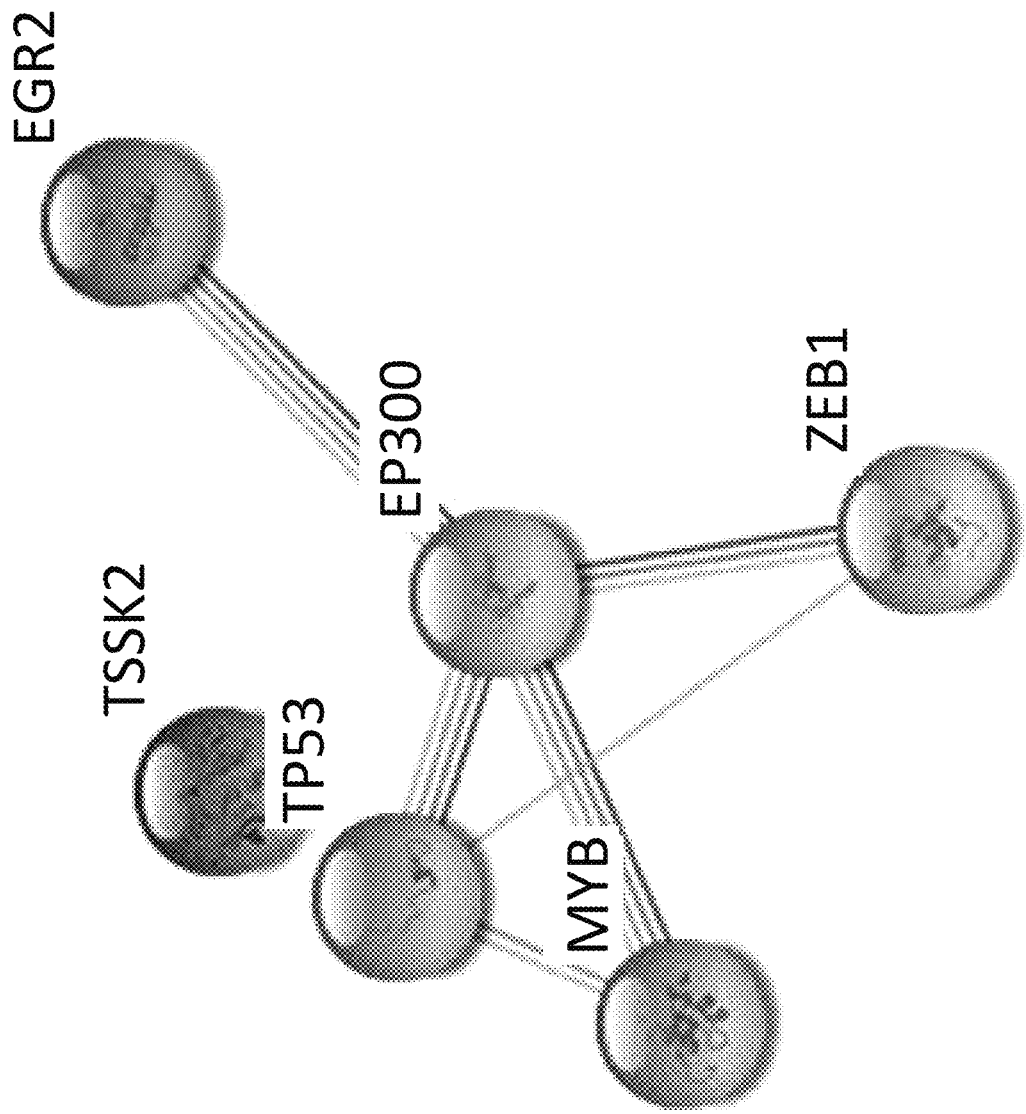
FIGS. 6A-6C. Most interesting predicted targets were networked using String online tool. (A) Most confirmed targets were related to TP53-negative regulation of cell cycle, pre-Notch transcription and translation and to factors involved in the development and production of platelets. (B) Most interesting target genes were associated to prion diseases, MAPK signalling pathway and P13K-Akt signalling pathway. (C) Proposed network for the interaction of α-synuclein, hsa-miR-150-5p and interesting target genes.
Figure 6B:
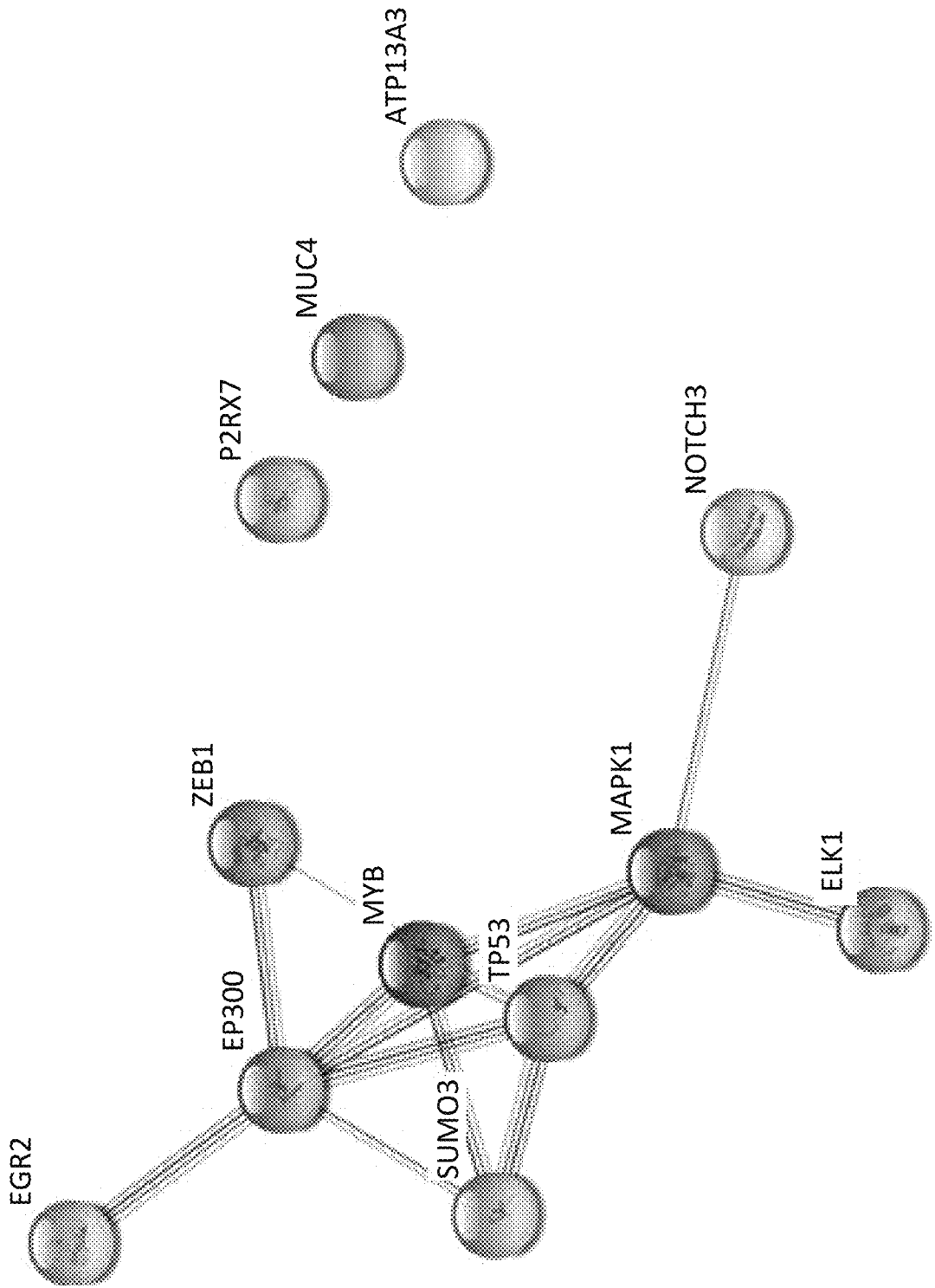
Figure 6C:
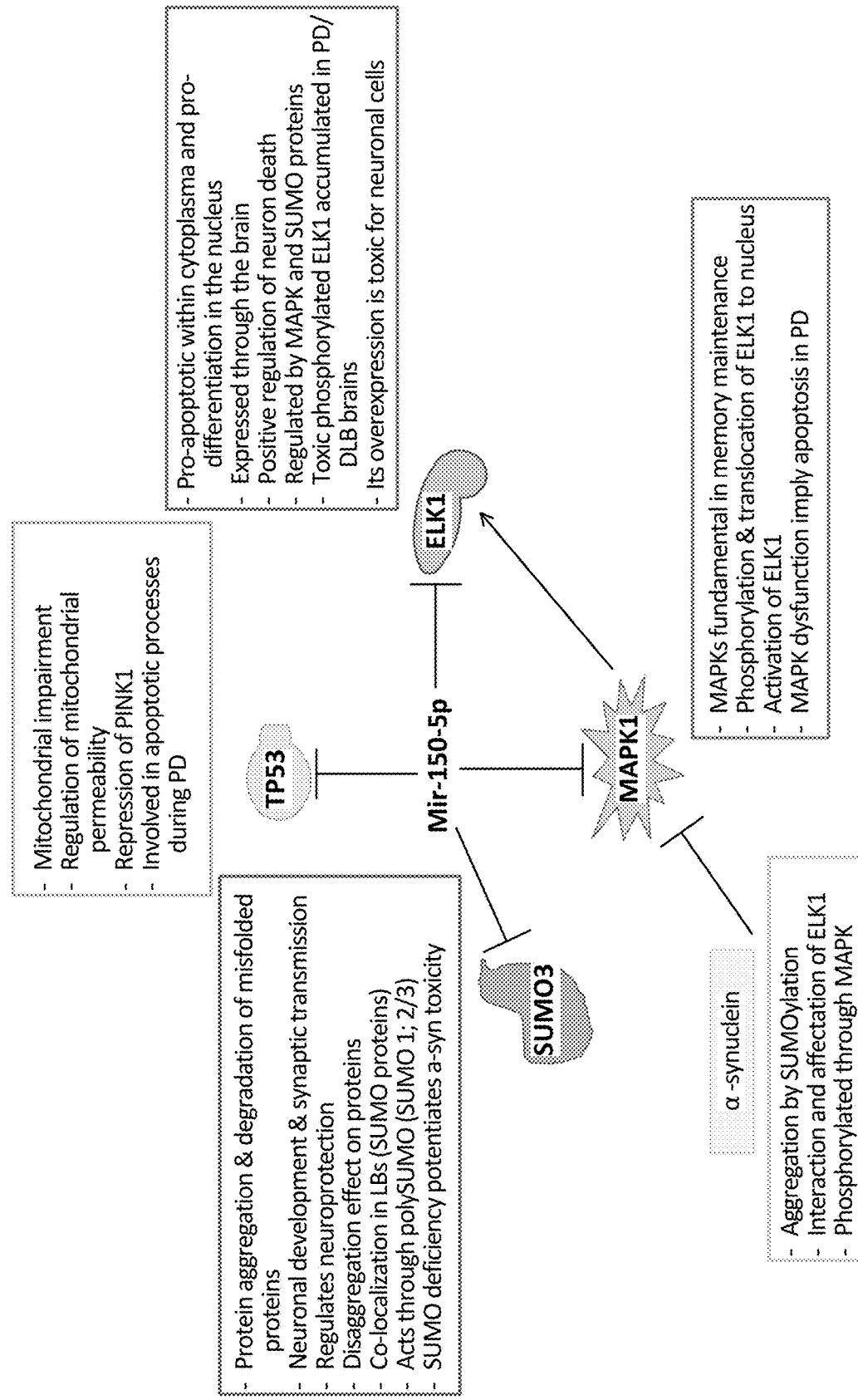
Figure 7A:
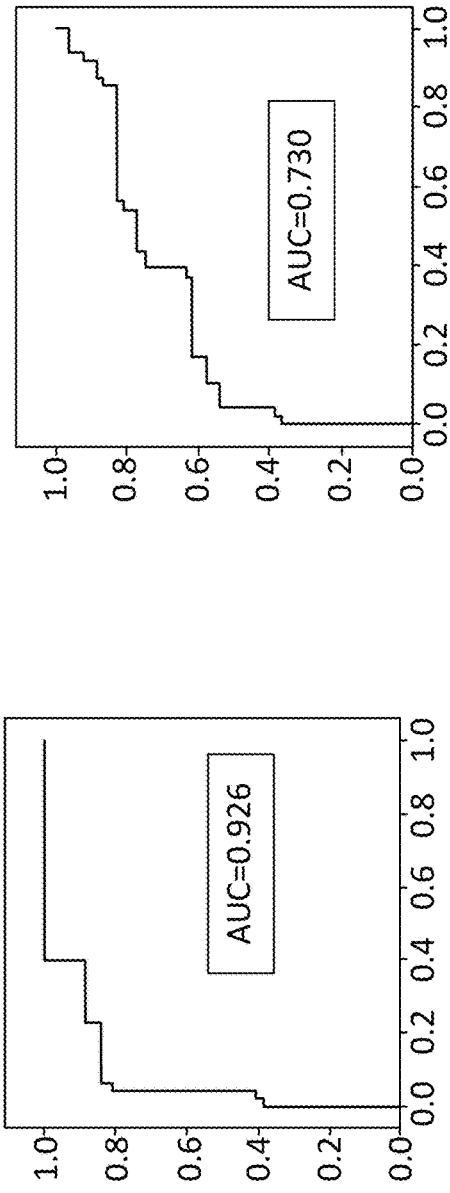
FIGS. 7A-7D. miRNA expression in platelets. ROC curves of the miRNAs: hsa-miR-150-5p, hsa-let-7d-5p, hsa-miR-26b-5p and hsa-miR-142-3p for the differentiation of DLB versus controls. X axis: specificity. Y axis: sensitivity.
Figure 7B:
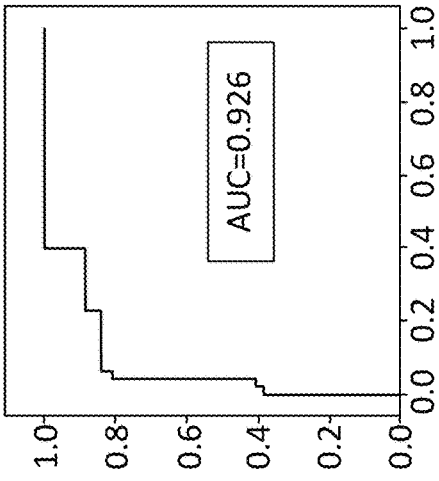
Figure 7C:
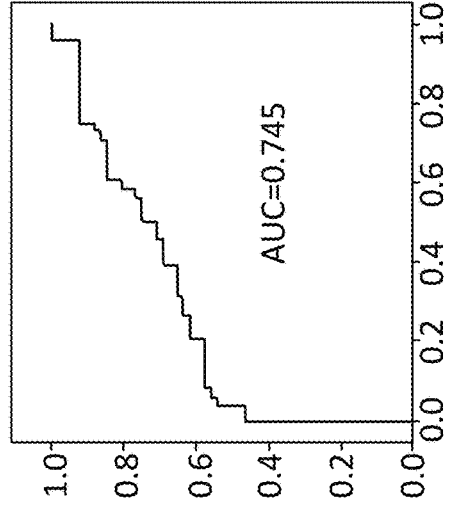
Figure 7D:
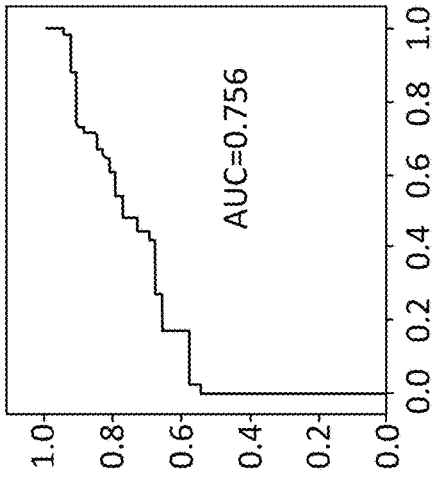
Figures 8G, 8H, 8I, 8J:
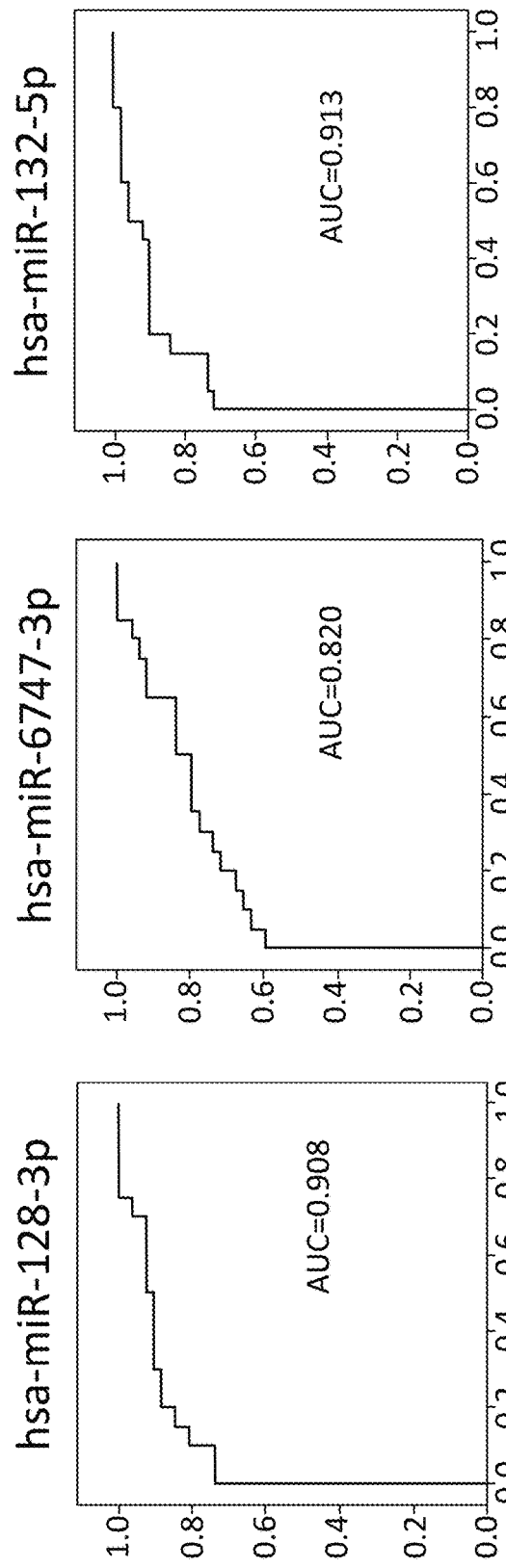
Figure 9:
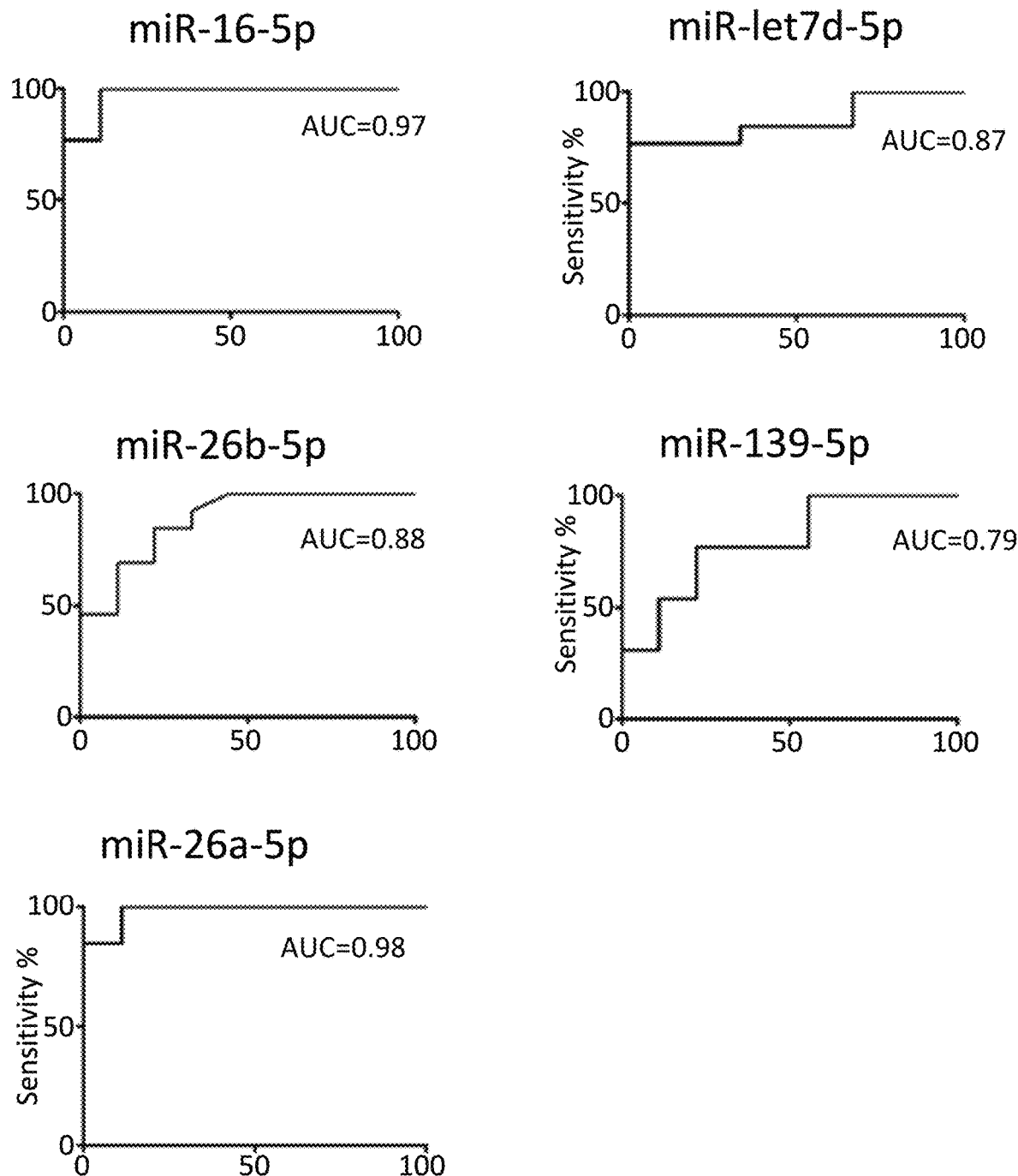
FIG. 9. miRNA expression in whole blood. ROC curves of the miRNAs: hsa-miR-16-5p, hsa-let-7d-5p, hsa-miR-26b-5p, hsa-miR-139-5p and hsa-miR-26a-5p for the differentiation of DLB versus AD. X axis: specificity. Y axis: sensitivity.
Figure 10:
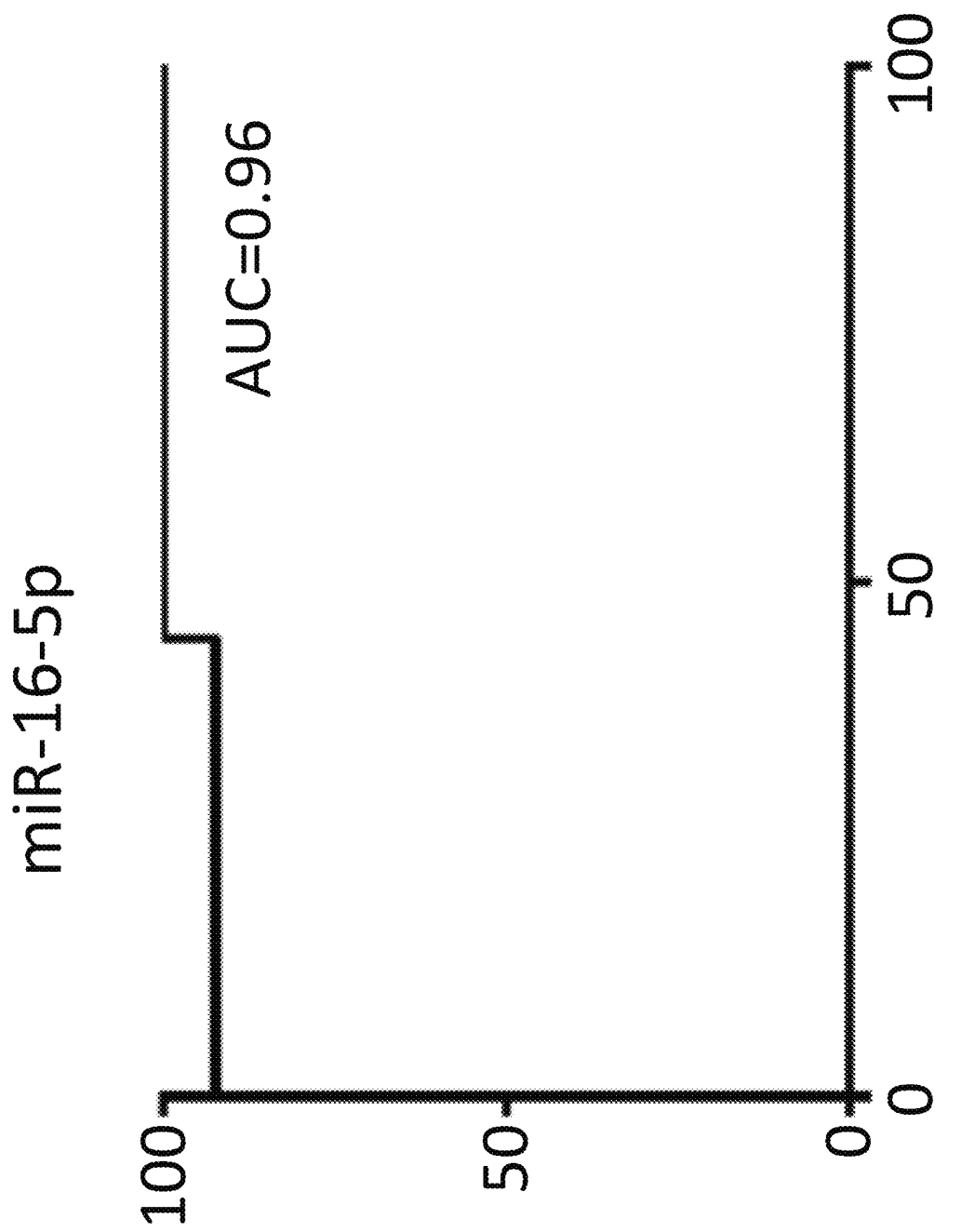
FIG. 10. miRNA expression in whole blood. ROC curve of hsa-miR-16-5p for the differentiation of PD versus AD. X axis: specificity. Y axis: sensitivity.

MiRGate online software was used for screening of specific predicted targets of hsa-miR-150-5p. Possible affected pathways were identified using DAVID software. The prediction revealed 5,787 target genes, but only 9 of them (MYB, P2RX7, EGR2, MUC4, ZEB1, ATP13A3, EP300, TP53, NOTCH3) were confirmed by independent tools (miRTarbase, Mirecords and OncomiRBD). These 9 target genes together with the most computational predicted ones (at least 4 different software identified them) were submitted to String online tool (https://string-db.org/) defining a small cluster involving 5 of our proteins and related to transcription factor activity and binding (p=0.03). Also, 5 of these proteins were associated to generation of neurons and regulation of neurogenesis by GO analysis for biological process (p=0.0381 in both cases). Reactome analysis defined these proteins as related to TP53-negative regulation of cell cycle (p=7.7·10$^{-5}$), pre-Notch transcription and translation (p=8.6·10$^{-5}$) and to factors involved in the development and production of platelets (p=1.4·10$^{-4}$) (FIG. 6A). Disease relation screening recognized an association of these genes to neuropathy (p=0.008) with high involvement in protein sumoylation processes and ubiquitin-protein ligase binding (maximum similarity score obtained—1—by DAVID online tool analysis). Bibliographic search in several data bases also revealed other target genes, including ELK1, SUMO3 and MAPK1, and their association to prion diseases (p=0.00252), MAPK signalling pathway (p=0.01) and P13K-Akt signalling pathway (p=0.0095) in a String-KEGG pathway analysis (FIG. 6B).

Example 14. Validation Results for the miR-150-5p in Platelets Samples

In the validation study, 16 DLB, 14 AD, 20 PD patients and 14 control individuals were included in the analysis. The results of this study were analysed altogether, after joint normalization of all samples (total: 162; comprising 59 DLB patients, 24 PD patients, 28 AD patients and 51 control individuals).

Figure 11:
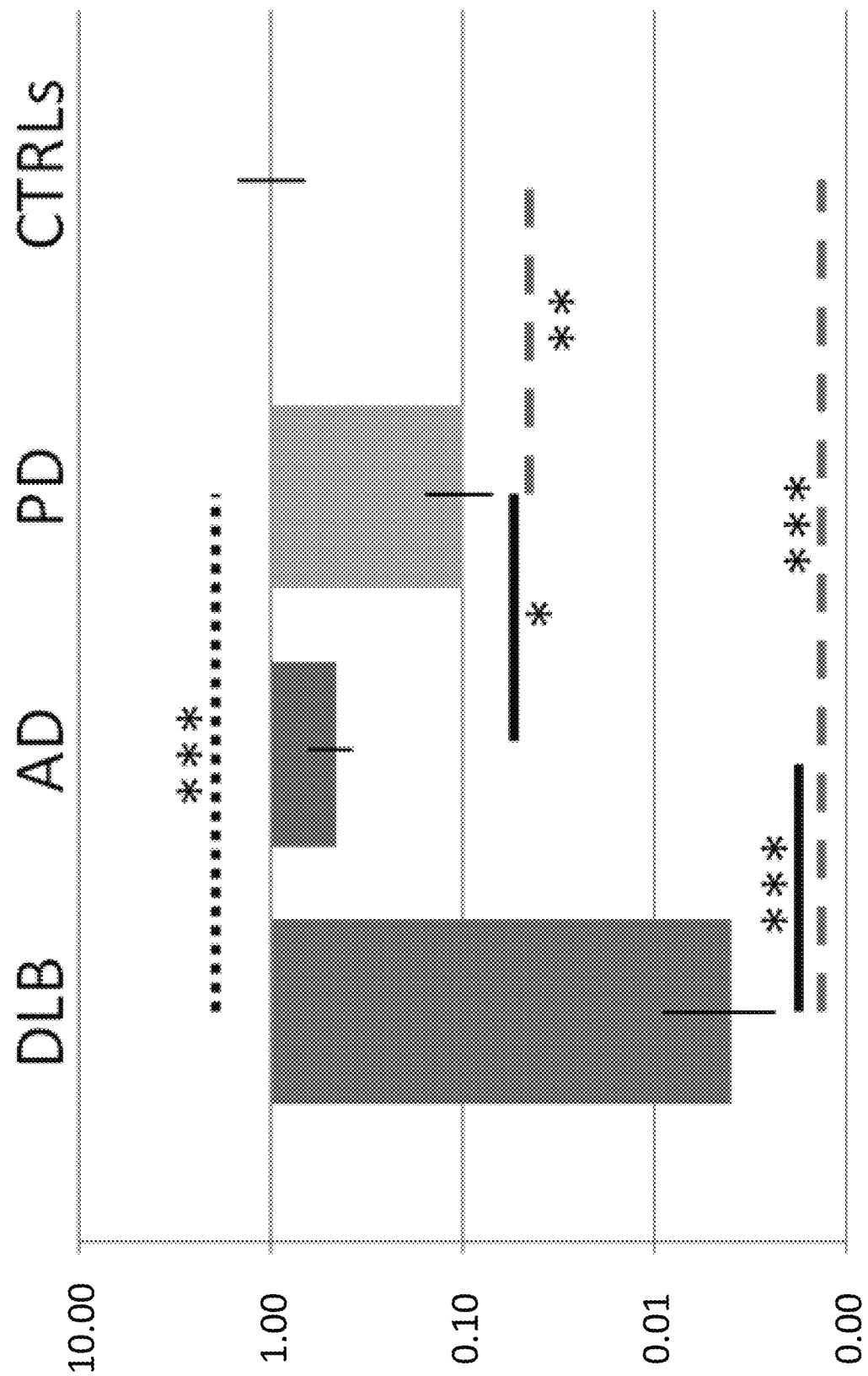
FIG. 11. miR-150-5p expression levels in platelets of DLB, AD and PD patients in comparison with controls. Black line, differences between DLB or PD and AD; dashed line, differences between DLB or PD and controls; dotted line, differences between DLB and PD.*p<0.05;p>0.01; *p>0.001. Differences were assessed with the Wilcoxon-Mann-Whitney test.

Such as it can be seen in FIG. 11, relevant results were obtained, especially for miR-150-5p.

FIG. 11 shows a statistically significant reduced level of miR-150-5p in platelets isolated from DLB and PD patients (i.e. patients suffering from a synucleinopathy) as compared with healthy control. This means that miR-150-5p is a strong biomarker for the diagnosis of synucleinopathies.

Moreover, FIG. 11 shows a statistically significant reduced level of miR-150-5p in platelets isolated from DLB and PD patients (i.e. patients suffering from a synucleinopathy) as compared with AD patients. This means that miR-150-5p is a strong biomarker for the differential diagnosis of synucleinopathies versus AD.

Figure 12:
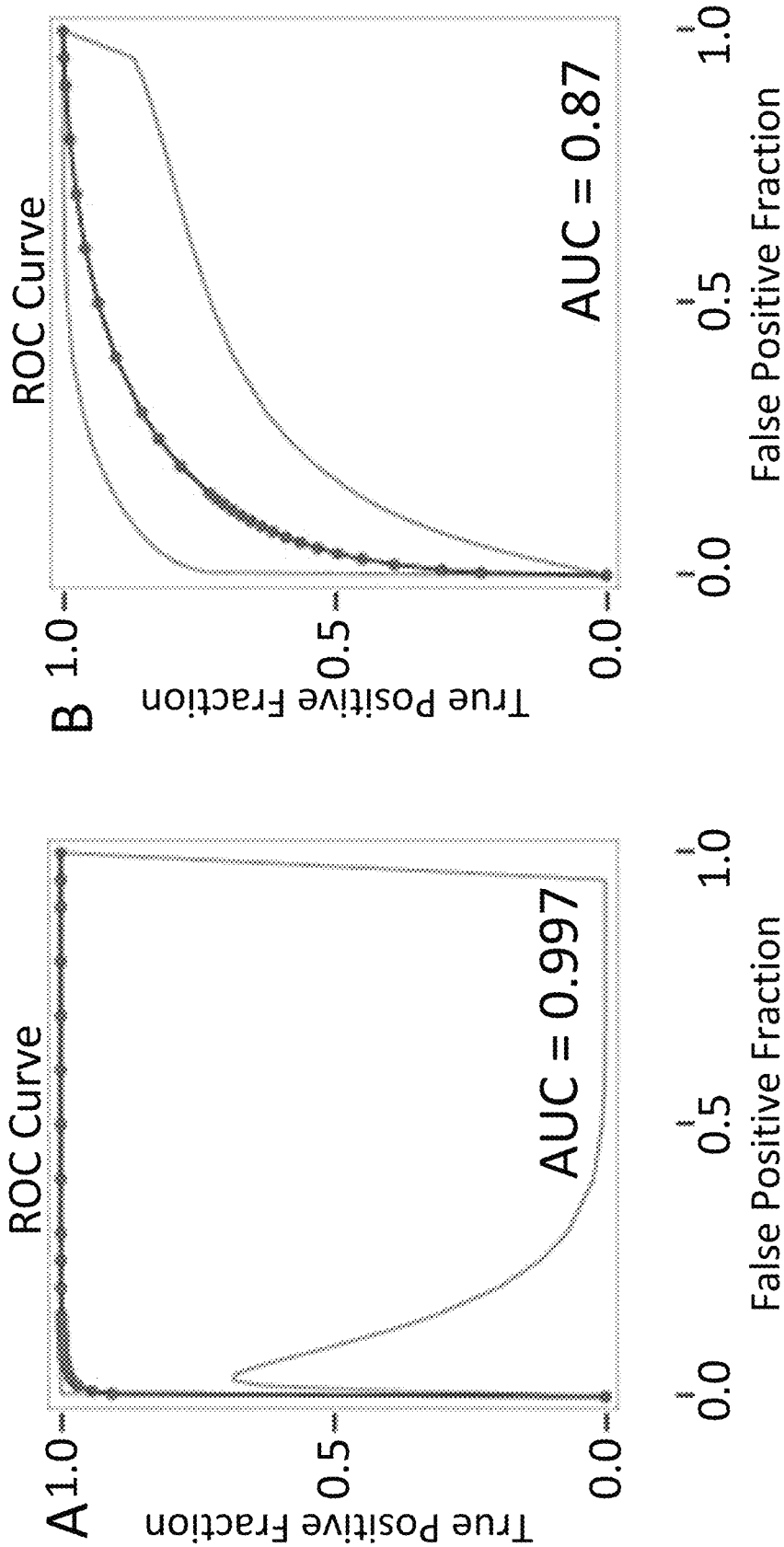
FIGS. 12A-12B. ROC curve analysis of miR-150-5p expression. (A) DLB patients vs controls. (B) Patients with synucleinopathy vs Alzheimer patients.

These results are confirmed by ROC curves shown in FIG. 12.

Example 15. Validation Results for Other miRNAs

Additionally, miRNAs shown in Table 2 are significantly diminished in DLB in comparison with AD.

TABLE 2

|   | let-7d-5p | miR-128-3p | miR-132-5p | miR-139-5p | miR-142-3p | miR-146a-5p | miR-25-3p | miR-26b-5p | miR-6747-3p |
|---|---|---|---|---|---|---|---|---|---|
| DLB vs AD | 0.14 0.03-0.62 p = 0.006 | 0.19 0.06-0.61 p = 0.03 | 0.12 0.04-0.42 p = 0.0015 | 0.16 0.04-0.70 p = 0.02 | 0.07 0.01-0.35 p = 0.00047 | 0.07 0.02-0.22 p = 0.00035 | 0.13 0.04-0.42 p = 0.0019 | 0.09 0.01-0.68 p = 0.0014 | 0.22 0.07-0.68 p = 0.019 |

Differences in miRNA expression between DLB and AD

The values in the first line of Table 2 represent the relative expression change of each miRNA in DLB vs AD obtained by the deltadeltaCt method. Values below 0.5 represent diminished expression in comparison with the other group (in this case AD). The values in the second line represent the deviation rage. p-value represented in the third line was obtained with the Wilcoxon-Mann-Whitney test.

Example 16. miRNAs Increased in Platelets of AD Patients with Respect to Healthy Controls Six miRNAs were significantly increased in AD when compared to healthy controls. This means that any of the miRNAs included in Table 3, or combinations thereof, could be used for the diagnosis of AD. So, the present invention also refers to an in vitro method for the diagnosis of AD, which comprises determining the expression level of at least one miRNA included in Table 3, or combination thereof, isolated from platelets obtained from the patient, wherein an increased expression level of at least one of the miRNAs included in Table 3, as compared with the expression level measured in healthy control subjects, is an indication that the patient is suffering from AD.

TABLE 3

|   | miR-132-5p | miR-142-3p | miR-146a-5p | miR-25-3p | miR-26b-5p | miR-6747-3p |
|---|---|---|---|---|---|---|
| AD vs CTRLs | 3.5 2.92-4.2 p = 0.000063 | 2.09 1.99-2.21 p = 0.028 | 5.00 3.03-8.27 p = 0.00013 | 3.76 2.38-5.93 p = 0.00026 | 1.90 1.57-2.30 p = 0.0036 | 3.5 2.40-5.10 p = 0.0006 |

Differences in miRNA expression between AD and controls.

The values in the first line of Table 3 represent the relative expression change of each miRNA in AD vs heathy controls and were obtained by the deltadeltaCt method. Values higher than 1.5 represent increased expression in comparison with the other group (in this case controls). The values in the second line represent the deviation rage. p-value represented in the third line were obtained with the Wilcoxon-Mann-Whitney test.

Example 17. miRNAs Decreased in Platelets from DLB Patients with Respect to PD Patients On the other hand, two miRNAs shown in Table 4 were significantly decreased in DLB when compared to PD patients. These could therefore serve as diagnostic markers to differentiate DLB from PD patients. So, the present invention also refers to an in vitro method for the differential diagnosis of DLB from PD, which comprises determining the expression level of at least one miRNA included in Table 4, or combination thereof, isolated from platelets obtained from the patient, wherein a decreased expression level of at least one of the miRNAs included in Table 4, as compared with the expression level of measured in PD patients, is an indication that the patient is suffering from DLB and not from PD.

TABLE 4

|   | miR-142-3p | miR-26b-5p | miR-150-5p |
|---|---|---|---|
| DLB vs PD | 0.12 0.02-0.97 p = 0.037 | 0.11 0.02-0.86 p = 0.0077 | 0.04 0.01-0.14 p = 0.00003 |

Diferences in miRNA expression between DLB and PD.

The values in the first line of Table 4 represent the relative expression change of each miRNA in DLB vs PD and were obtained by the deltadeltaCt method. Values below 0.5 represent diminished expression in comparison with the other group (in this case PD). The values in the second line represent the deviation rage. p-value represented in the third line were obtained with the Wilcoxon-Mann-Whitney test.

The invention claimed is:
1. A method of treating a patient having a synucleinopathy or having an elevated risk for developing a synucleinopathy, the method comprising administering a therapeutic selected from the group consisting of a precursor of dopamine, a dopamine agonist, a monoamine oxidase-B (MAO-B)

inhibitor and an alpha-synuclein anti-aggregation compound to a patient having reduced expression of miR-150-5p, as compared to an expression level of miR-150-5p in platelets obtained from one or more healthy human subjects, wherein the miR-150-5p expression level has been determined by a method comprising:
   (i) obtaining platelet-enriched pellets from the patient;
   (ii) extracting microRNAs (miRNAs) from the platelet-enriched pellets;
   (iii) reverse transcribing the miRNAs extracted from the platelet-enriched pellets into cDNAs;
   (iv) amplifying the cDNAs;
   (v) measuring an expression level of miR-150-5p in the amplified cDNAs; and
   (vi) detecting a reduced expression level of miR-150-5p, as compared to the expression level of miR-150-5p in platelets obtained from the one or more healthy human subjects.

2. The method of treating a patient of claim 1, wherein the synucleinopathy is Dementia with Lewy bodies or Parkinson's disease.

3. The method of treating a patient of claim 1, wherein the dopamine precursor comprises levodopa.

4. The method of treating a patient of claim 3, wherein the dopamine precursor is administered in combination with a dopa decarboxylase inhibitor or a COMT inhibitor.

5. The method of treating a patient of claim 4, wherein the synucleinopathy is Parkinson's disease.

6. The method of treating a patient of claim 1, wherein the MAO-B inhibitor is selected from the group consisting of safinamide, selegiline and rasagiline.

7. The method of treating a patient of claim 1, wherein the alpha-synuclein anti-aggregation compound is selected from the group consisting of BIIB054, NPT200-11/UCB0599, PRX002/RO7046015 and NPT088.

8. The method of claim 1, further comprising measuring the expression levels of at least one miRNA selected from the group consisting of miR-7d-5p, miR-142-3p, miR-26b-5p, miR-139-5p, miR-146a-5p, miR-128-3p, miR-6747-3p, miR-132-5p, miR-25-3p, hsa-miR-16-5p, hsa-miR-26a-5p, and a combination thereof.

9. The method of treating a patient of claim 8, wherein the synucleinopathy is Dementia with Lewy bodies or Parkinson disease.

10. The method of treating a patient of claim 1, further comprising performing diagnostic imaging.

11. The method of treating a patient of claim 10, wherein the diagnostic imaging comprises amyloid PET scan.

12. The method of treating a patient of claim 1, further comprising determination of phosphorylated tau/amyloid beta 1-42 ratio in cerebrospinal fluid of the patient.

13. The method of treating a patient of claim 1, wherein the patient having an elevated risk for developing a synucleinopathy is an idiopathic rapid eye movement sleep behavior disorder (iRBD) patient, a patient with hyposmia, or a leucine-rich repeat kinase-2 (LRKK2) mutation carrier.

14. A method of treating a patient suspected of having a synucleinopathy or suspected of having an elevated risk for developing a synucleinopathy, the method comprising:
   (a) obtaining microRNA (miRNA) expression data from platelet-enriched pellets obtained from the patient by a method comprising:
      (i) extracting microRNAs from the platelet-enriched pellets;
      (ii) reverse transcribing the miRNAs extracted from the platelet-enriched pellets into cDNAs;
      (iii) amplifying the cDNAs;
      (iv) measuring expression levels of miR-150-5p in the amplified cDNAs;
      (v) detecting a reduced expression level of miR-150-5p, as compared to an expression level of miR-150-5p in platelets obtained from one or more patients diagnosed as having Alzheimer's disease; and
   (b) administering a therapeutic selected from the group consisting of a precursor of dopamine, a dopamine agonist, a monoamine oxidase-B (MAO-B) inhibitor and an alpha-synuclein anti-aggregation compound, and not a neuroleptic agent, to the patient having reduced expression of miR-150-5p, as compared to the expression level of miR-150-5p in the platelets obtained from the one or more patients diagnosed as having Alzheimer's disease.

15. The method of treatment of claim 14, wherein the synucleinopathy is Dementia with Lewy bodies or Parkinson disease.

16. The method of treatment of claim 14, further comprising measuring the expression levels of at least one miRNA selected from the group consisting of hsa-let-7d-5, miR-142-3p, miR-26b-5p, miR-139-5p, miR-146a-5p, miR-128-3p, hsa-miR-6747-3, miR-132-5p, miR-25-3p, hsa-miR-16-5p, hsa-miR-26a-5p, and a combination thereof.

17. The method of treatment of claim 16, wherein the synucleinopathy is Dementia with Lewy bodies or Parkinson disease.

18. The method of treatment of claim 14, further comprising performing diagnostic imaging.

19. The method of treatment of claim 18, wherein the diagnostic imaging comprises amyloid PET scan.

20. The method of treatment of claim 14, further comprising determination of phosphorylated tau/amyloid beta 1-42 ratio in cerebrospinal fluid of the patient.

21. The method of treatment of claim 14, wherein the patient having an elevated risk for developing a synucleinopathy is an iRBD patient, a patient with hyposmia, or a LRRK2 mutation carrier.

22. The method of treatment of claim 14, wherein the dopamine precursor comprises levodopa.

23. The method of treatment of claim 22, wherein the dopamine precursor is administered in combination with a dopa decarboxylase inhibitor or a COMT inhibitor.

24. The method of treatment of claim 23, wherein the synucleinopathy is Parkinson's disease.

25. The method of treatment of claim 14, wherein the MAO-B inhibitor is selected from the group consisting of safinamide, selegiline and rasagiline.

26. The method of treatment of claim 14, wherein the alpha-synuclein anti-aggregation compound is selected from the group consisting of BIIB054, NPT200-11/UCB0599, PRX002/RO7046015 and NPT088.

* * * * *